United States Patent [19]

Chen et al.

[11] Patent Number: 4,870,199

[45] Date of Patent: Sep. 26, 1989

[54] **PROCESSES FOR THE SYNTHESIS OF DIPROTECTED R[R*,S*]-3,5-DIHYDROXY-6-OXOHEXANOATE ESTERS**

[75] Inventors: Kau-Ming Chen, Randolph; Goetz E. Hardtmann, Morristown; Prasad K. Kapa, Parsippany; George T. Lee, Bloomfield; Jerome Linder, Westfield; Sompong Wattanasin, Hopatcong, all of N.J.

[73] Assignee: Sandoz Pharm. Corp., E. Hanover, N.J.

[21] Appl. No.: 166,594

[22] Filed: Mar. 10, 1988

Related U.S. Application Data

[63] Continuation-in-part of Ser. No. 857,689, Apr. 30, 1986, abandoned, and a continuation-in-part of Ser. No. 23,079, Mar. 6, 1987, abandoned.

[51] Int. Cl.$^4$ .............................................. C07F 7/18
[52] U.S. Cl. ..................................... 556/437; 560/23; 560/53; 560/61; 560/174; 560/177; 560/186; 552/105
[58] Field of Search ........................ 260/395; 556/437; 560/23, 53, 61, 177, 186, 174

[56] References Cited

U.S. PATENT DOCUMENTS

| | | | |
|---|---|---|---|
| 4,499,289 | 2/1985 | Baran et al. | 549/292 |
| 4,571,428 | 2/1986 | Kapa | 560/53 X |
| 4,611,068 | 9/1986 | Guindon et al. | 549/292 |
| 4,613,610 | 9/1986 | Wareing | 514/406 |
| 4,650,890 | 3/1987 | Jewell et al. | 560/174 X |
| 4,677,211 | 6/1987 | Jewell et al. | 548/491 |

OTHER PUBLICATIONS

March, Advanced Organic Chemistry, Second Edition, McGraw-Hill, New York (1977) pp. 443-445.
Chen et al. I, Tetrahedron Letters 28, 155-158 (1987).
Chen et al. II, 192nd. American Chemical Society National Meeting, Anaheim, California, Sep. 7-12, 1986.
Kapa et al., Tetrahedron Letters 25, 2435-2438 (1984).
Saito et al., Chemistry Letters 1984, 1389-1392.

*Primary Examiner*—Richard L. Raymond
*Attorney, Agent, or Firm*—Gerald D. Sharkin; Richard E. Vila; Melvyn M. Kassenoff

[57] ABSTRACT

Process for the synthesis of compounds of the formula

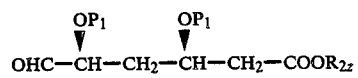

in R[R*,S*] enantiomeric form, wherein each
$P_1$ is independently an hydroxy group-protecting group, and
$R_{2z}$ is $C_{1-4}$alkyl, benzyl or allyl, comprising, as a key step when $R_{2z}$ is $R_{2x}$, the reaction of the compound of the formula

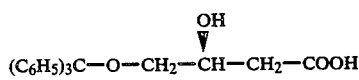

in (S) enantiomeric form with a compound of the formula

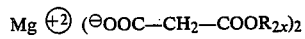

to obtain a compound of the formula

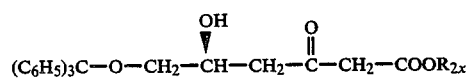

in (S) enantiomeric form, and, as a key step when $R_{2z}$ is $R_{2y}$, the reaction of a compound of the formula

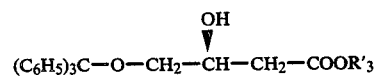

in (S) enantioimeric form with a compound of the formula

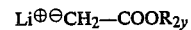

to obtain a compound of the formula

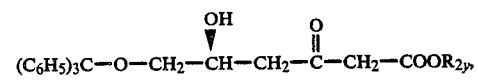

in (S) enantiomeric form, wherein
$R_{2x}$ is primary or secondary $C_{1-4}$alkyl, benzyl or allyl,
$R_{2y}$ is $C_{1-4}$alkyl not containing an asymmetric carbon atom, and
$R_3'$ is methyl or ethyl, processes for the synthesis of compounds of the formula

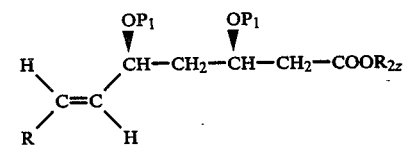

comprising reacting a compound of the formula

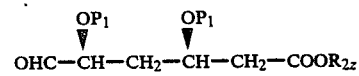

(Abstract continued on next page.)

with the reaction product of a strong base and a compound of the formula

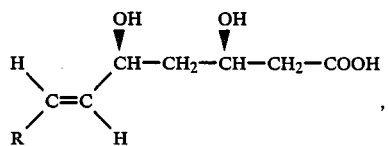

wherein each
$R_7$ is methyl or ethyl,
R is as defined in the specification, and each
$P_1$ independently and $R_{2z}$ are as defined above, and
the compounds of the formula

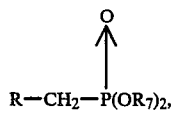

wherein R and each $R_7$ are as defined above.

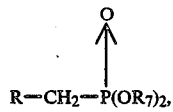

optionally followed by, when $R_{2z}$ is allyl, cleavage of the allyl and $P_1$ groups to obtain the corresponding compound of the formula 12 Claims, No Drawings

PROCESSES FOR THE SYNTHESIS OF DIPROTECTED R[R*,S*]-3,5-DIHYDROXY-6-OXOHEXANOATE ESTERS

This continuation-in-part of application Ser. No. 857,689, filed Apr. 30, 1986 and now abandoned and a continuation-in-part of application Ser. No. 023,079, filed Mar. 6, 1987 and now abandoned, said application Ser. No. 023,079 also being a continuation-in-part of said application Ser. No. 857,689.

This invention is directed to processes for the synthesis of compounds of the formula

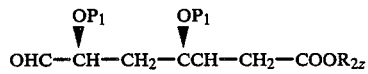
(II)

in R[R*,S*], i.e., 3R,5S, enantiomeric form, wherein each $R_1$ is independently an hydroxy group-protecting group, and $R_{2z}$ is $C_{1-4}$alkyl, benzyl or allyl, compounds of the formula

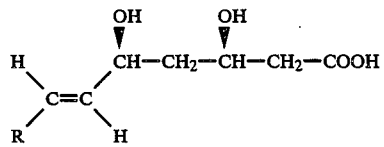
(III)

and intermediates in the synthesis of compounds of the formula

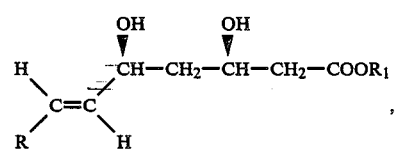
(I)

wherein $R_1$ is hydrogen, $R_2$ or M, wherein $R_2$ is a physiologically acceptable and hydrolyzable ester group, and M is a pharmaceutically acceptable cation, and R is a group of Formula A, B, C, D, E, Fa, Fb, Fc, G or H, i.e.,

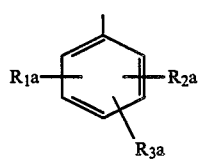
(A)

wherein each of $R_{1a}$, $R_{2a}$ and $R_{3a}$ is independently hydrogen; halo; $C_{1-4}$alkyl; $C_{1-4}$haloalkyl; phenyl; phenyl substituted by halo, $C_{1-4}$alkoxy, $C_{2-8}$alkanoyloxy, $C_{1-4}$alkyl or $C_{1-4}$haloalkyl; or $-OR^3$ in which $R^d$ is hydrogen, $C_{2-8}$alkanoyl, benzoyl, phenyl, halophenyl, phenyl($C_{1-3}$alkyl), $C_{1-9}$alkyl, cinnamyl, $C_{1-4}$haloalkyl, allyl, cycloalkyl($C_{1-3}$alkyl), adamantyl($C_{1-3}$alkyl) or substituted phenyl($C_{1-3}$alkyl) each substituent of which is selected from the group consisting of halo, $C_{1-4}$alkoxy, $C_{1-4}$alkyl and $C_{1-4}$haloalkyl (the halogen atoms including fluoro and chloro and cycloalkyl including cyclohexyl);

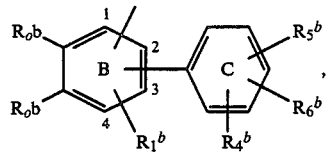
(B)

wherein the two $R_ob$ groups together form a radical of the formula

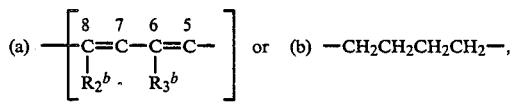

wherein $R_2^b$ is hydrogen, $C_{1-3}$alkyl, n-butyl, i-butyl, $C_{1-3}$alkoxy, n-butoxy, i-butoxy, trifluoromethyl, fluoro, chloro, phenoxy or benzyloxy;

$R_3^b$ is hydrogen, $C_{1-3}$alkyl, $C_{1-3}$alkoxy, trifluoromethyl, fluoro, chloro, phenoxy or benzyloxy, with the provisos that not more than one of $R_2^b$ and $R_3^b$ is trifluoromethyl, not more than one of $R_2^b$ and $R_3^b$ is phenoxy, and not more than one of $R_2^b$ and $R_3^b$ is benzyloxy;

$R_1^b$ is hydrogen, $C_{1-3}$alkyl, fluoro, chloro or benzyloxy;

$R_4^b$ is hydrogen, $C_{1-3}$alkyl, n-butyl, i-butyl, $C_{1-3}$alkoxy, n-butoxy, i-butoxy, trifluoromethyl, fluoro, chloro, phenoxy or benzyloxy;

$R_5^b$ is hydrogen, $C_{1-3}$alkyl, $C_{1-3}$alkoxy, trifluoromethyl, fluoro, chloro, phenoxy or benzyloxy, with the provisos that not more than one of $R_4^b$ and $R_5^b$ is trifluoromethyl, not more than one of $R_4^b$ and $R_5^b$ is phenoxy, and not more than one of $R_4^b$ and $R_5^b$ is benzyloxy; and $R_6^b$ is hydrogen, $C_{1-2}$alkyl, $C_{1-2}$alkoxy, fluoro or chloro;

with the proviso that the free valence on ring B and ring C are ortho to each other;

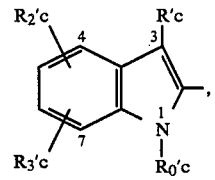
(C)

wherein one of $R'c$ and $R_o'c$ is

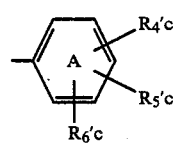

and the other is $C_{1-3}$alkyl, n-butyl or i-butyl, wherein

R$_4$'c is hydrogen, C$_{1-3}$alkyl, n-butyl, i-butyl, C$_{1-3}$alkoxy, n-butoxy, i-butoxy, trifluoromethyl, fluoro, chloro, phenoxy or benzyloxy;

R$_5$'c is hydrogen, C$_{1-3}$alkyl, C$_{1-3}$alkoxy, trifluoromethyl, fluoro, chloro, phenoxy or benzyloxy, with the provisos that not more than one of R$_4$'c and R$_5$'c is trifluoromethyl, not more than the one of R$_4$'c and R$_5$'c is phenoxy, and not more than one of R$_4$'c and R$_5$'c is benzyloxy; and R$_6$'c is hydrogen, C$_{1-2}$alkyl, C$_{1-2}$alkoxy, fluoro or chloro;

R$_2$'c is hydrogen, C$_{1-3}$alkyl, n-butyl, i-butyl, C$_{1-3}$alkoxy, n-butoxy, i-butoxy, trifluoromethyl, fluoro, chloro, phenoxy or benzyloxy; and R$_3$'c is hydrogen, C$_{1-3}$alkyl, C$_{1-3}$alkoxy, trifluoromethyl, fluoro, chloro, phenoxy or benzyloxy;

with the provisos that not more than one of R$_2$'c and R$_3$'c is trifluoromethyl, not more than one of R$_2$'c and R$_3$'c is phenoxy, and not more than one of R$_2$'c and R$_3$'c is benzyloxy;

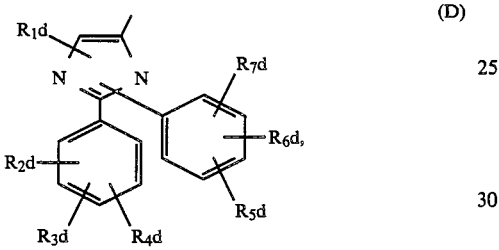

(D)

wherein

R$_1$d is C$_{1-6}$alkyl not containing an asymmetric carbon atom;

each of R$_2$d and R$_5$d is independently hydrogen, C$_{1-3}$alkyl, n-butyl, i-butyl, t-butyl, C$_{1-3}$alkoxy, n-butoxy, i-butoxy, trifluoromethyl, fluoro, chloro, phenyl, phenoxy or benzyloxy;

each of R$_3$d and R$_6$d is independently hydrogen, C$_{1-3}$alkyl, C$_{1-3}$alkoxy, trifluoromethyl, fluoro, chloro, phenoxy or benzyloxy; and each of R$_4$d and R$_7$d is independently hydrogen, C$_{1-2}$alkyl, C$_{1-2}$alkoxy, fluoro or chloro;

with the provisos that not more than one of R$_2$d and R$_3$d is trifluoromethyl, not more than one of R$_2$d and R$_3$d is phenoxy, not more than one of R$_2$d and R$_3$d is benzyloxy, not more than one of R$_5$d and R$_6$d is trifluoromethyl, not more than one of R$_5$d and R$_6$d is phenoxy, and not more than one of R$_5$d and R$_6$d is benzyloxy;

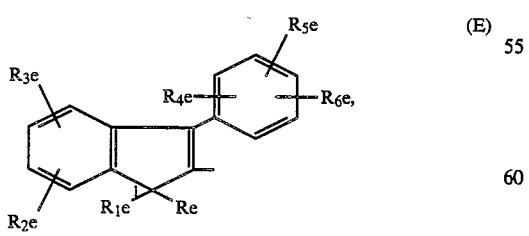

(E)

wherein

Re is hydrogen or primary or secondary C$_{1-6}$alkyl not containing an asymmetric carbon atom, and R$_1$e is primary or secondary C$_{1-6}$alkyl not containing an asymmetric carbon atom or Re and R$_1$e taken together are —(CH$_2$)$_m$— or (Z)—CH$_2$—CH=CH—CH$_2$—, wherein m is 2, 3, 4, 5 or 6;

R$_2$e is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy or benzyloxy;

R$_3$e is hydrogen, C$_{1-3}$alkyl, C$_{1-3}$alkoxy, trifluoromethyl, fluoro, chloro, phenoxy or benzyloxy, with the provisos that not more than one of R$_2$e and R$_3$e is trifluoromethyl, not more than one of R$_2$e and R$_3$e is phenoxy, and not more than one of R$_2$e and R$_3$e is benzyloxy;

R$_4$e is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy or benzyloxy;

R$_5$e is hydrogen, C$_{1-3}$alkyl, C$_{1-3}$alkoxy, trifluoromethyl, fluoro, chloro, phenoxy or benzyloxy; and R$_6$e is hydrogen, C$_{1-2}$alkyl, C$_{1-2}$alkoxy, fluoro or chloro; with the provisos that not more than one of R$_4$e and R$_5$e is trifluoromethyl, not more than one of R$_4$e and R$_5$e is phenoxy, and not more than one of R$_4$e and R$_5$e is benzyloxy;

(F)

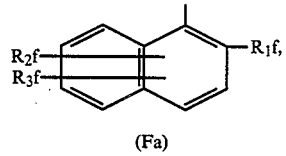

(Fa)

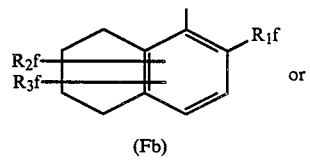

or (Fb)

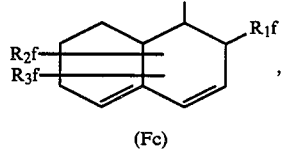

, (Fc)

wherein each of R$_1$f, R$_2$f and R$_3$f is independently fluoro, chloro, hydrogen or C$_{1-4}$alkyl, R$_1$f preferably being methyl;

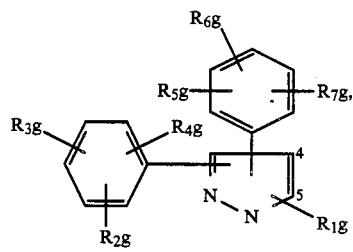

(G)

wherein

R$_1$g is C$_{1-6}$alkyl not containing an asymmetric carbon atom;

each of R$_2$g and R$_5$g is independently hydrogen, C$_{1-3}$alkyl, n-butyl, i-butyl, t-butyl, C$_{1-3}$alkoxy, n-butoxy, i-butoxy, trifluoromethyl, fluoro, chloro, phenyl, phenoxy or benzyloxy;

each of $R_{3g}$ and $R_{6g}$ is independently hydrogen, $C_{1-3}$alkyl, $C_{1-3}$alkoxy, trifluoromethyl, fluoro, chloro, phenoxy or benzyloxy; and each of $R_{4g}$ and $R_{7g}$ is independently hydrogen, $C_{1-2}$alkyl, $C_{1-2}$alkoxy, fluoro or chloro; with the provisos that not more than one of $R_{2g}$ and $R_{3g}$ is trifluoromethy, not more than one of $R_{2g}$ and $R_{3g}$ is phenoxy, not more than one of $R_{2g}$ and $R_{3g}$ is benzyloxy, not more than one of $R_{5g}$ and $R_{6g}$ is trifluoromethyl, not more than one of $R_{5g}$ and $R_{6g}$ is phenoxy, and not more than one of $R_{5g}$ and $R_{6g}$ is benzyloxy; with the provisos that (i) the free valence is in the 4- or 5-position of the pyrazole ring, and (ii) $R_{1g}$ and the free valence are ortho to each other; or

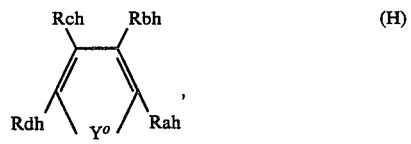

wherein

Rah is a free valence, Rbh is $R_2H$, Rch is $R_3h$, Rdh is $R_4h$ and Y° is

or

Rah is $R_1h$, Rbh is a free valence, Rch is $R_2h$, Rdh is $R_3h$ and Y° is O, S or

$R_1h$, $R_2h$, $R_3h$ and $R_4h$ independently are $C_{1-6}$alkyl not containing an asymmetric carbon atom, $C_{3-7}$cycloalkyl or

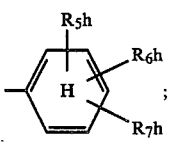

or in the case of $R_3h$ and $R_4h$ additionally hydrogen, or, for $R_3h$ when Y° is O or S,

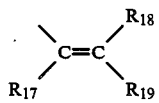

wherein $R_{17}$ is hydrogen or $C_{1-3}$alkyl, and $R_{18}$ and $R_{19}$ are independently hydrogen, $C_{1-3}$alkyl or phenyl; each $R_5h$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy; each $R_6h$ is independently hydrogen, $C_{1-3}$alkyl, $C_{1-3}$alkoxy, trifluoromethyl, fluoro, chloro, bromo, phenoxy or benzyloxy, and each $R_7h$ is independently hydrogen, $C_{1-2}$alkyl, $C_{1-2}$alkoxy, fluoro or chloro, with the proviso that there may only be one each of trifluoromethyl, phenoxy and benzyloxy on each ring H.

R is, for example, a group of Formula A, B wherein $R_6{}^b$ is hydrogen, C wherein $R_6{}'c$ is hydrogen, D, E, Fa, Fb, Fc or G.

The compounds of Formula I may be divided into seven grups, i.e., Groups IA-IH, depending upon the significance of R, viz.:

IA when R=A,
IB when R=B,
IC when R=C,
ID when R=D,
IE when R=E,
IF when R=Fa, Fb or Fc,
IG when R=G and
IH when R=H.

The compounds of Formula I as well as those of Groups IA-IH may be divided into twenty-seven subgroups depending upon the significance of $R_1$, viz.:

| Subgroup | Compounds of Formula or Group | Wherein $R_1$ is |
| --- | --- | --- |
| $I_1$ | I | $R_2$ |
| $I_2$ | I | M |
| $I_3$ | I | H |
| $IA_1$ | IA | $R_2$ |
| $IA_2$ | IA | M |
| $IA_3$ | IA | H |
| $IB_1$ | IB | $R_2$ |
| $IB_2$ | IB | M |
| $IB_3$ | IB | H |
| $IC_1$ | IC | $R_2$ |
| . | . | . |
| . | . | . |
| . | . | . |
| $IH_3$ | IH | H |

The compounds of Formula I, the corresponding δ-lactones, processes for converting a compound of Formula I wherein $R_1$ has one significance into the corresponding compound wherein it has a different significance and/or into the corresponding δ-lactone are known. See, for example:

R=A: U.S. Pat. Nos. 4,308,378 and 4,375,475
R=B: PCT Published Application WO 84/02903 and U.S. applications Ser. No. 06/570,584, filed Jan. 13, 1984 and now abandoned, and Serial No. 07/061,079, filed June 10, 1987 and now abandoned
P=C: PCT Published Application WO 84/02131 and U.S. application Ser. No. 06/722,288, filed Apr. 11, 1985 and now
R=D: U.S. Pat. No. 4,668,794 and PCT Published Application WO 86/07054
R=E: PCT Published Application Wo 86/03488 and U.S. applications Ser. No. 06/677,917, filed Dec. 4, 1984 and now abandoned, and Ser. No. 06/837,479, filed Mar. 7, 1986 and now abandoned
R=Fa, Fb or Fc: U.S. Pat. No. 4,474,971 (δ-lactone form only)
R=G: U.S. Pat. No. 4,613,610 and PCT Published Application WO 86/00307
R=H: PCT Published Application WO 87/02662 and U.S. applications Ser. No. 06/919,275, filed Oct. 15, 1986, and Ser. No. 06/945,428, filed Dec. 22, 1986 and now each of which is hereby incorporated by reference.

The compounds of Formula I and the corresponding δ-lactones are HMG-CoA reductase inhibitors, i.e., cholesterol biosynthesis inhibitors, and, therefore, they are useful for the treatment of hyperlipoproteinemia and atherosclerosis as disclosed in the aforementioned patents, published applications and applications which have been incorporated by reference.

The preferences for each of the variables in A, B, C, D, E, Fa, Fb, Fc, G and H are as set forth in the aforementioned patents, published applications and applications which have been incorporated by reference.

By the term "physiologically acceptable and hydrolyzable ester group" is meant a group, which together with the —COO— radical to which it is attached, forms an ester group which is physiologically acceptable and hydrolyzable under physiological conditions to yield a compound of Formula I wherein $R_1$ is hydrogen and an alcohol which itself is physiologically acceptable, i.e., non-toxic at the desired dosage level, particularly those which are free of centers of asymmetry. $R_2$ is preferably $R_2'$, where $R_2'$ is $C_{1-4}$alkyl or benzyl, especially $R_2''$, where $R_2''$ is $C_{1-3}$alkyl, b-butyl, i-butyl, t-butyl or benzyl, e.g., ethyl.

M is preferably an alkali metal cation or ammonium, preferably M', where M' is sodium or potassium, and especially sodium.

As set forth above, this invention is directed to processes for the synthesis of compounds of the formula

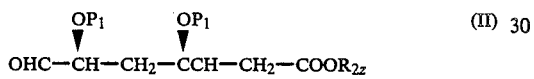

in R[R*,S*], i.e., 3R,5S, enantiomeric form utilizing L-malic acid ((S)-malic acid (Compound XI)) as the starting material as described in Reaction Scheme A. Each step of each process, each combination of two or more consecutive steps and each entire process are within the scope of this invention.

This invention is also directed to the synthesis of compounds of the formula

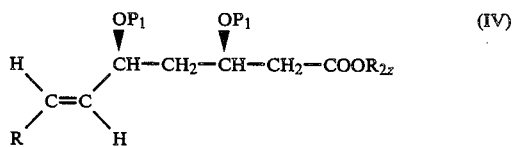

by reacting the reaction product of a strong base and a compound of the formula

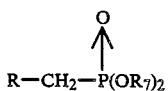

with a compound of the formula

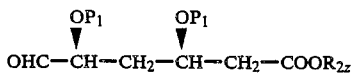

as set forth in further detail in Reaction Scheme B. The compounds of Formula V are also part of this invention.

When the strong base is an organolithium compound, e.g., a lower alkyllithium, preferably n-butyllithium, the reaction product of the strong base with the compound of Formula V is of the formula

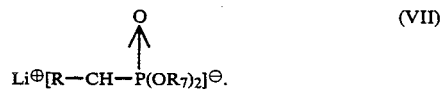

This process has the advantage over the conventional use of a non-phosphonate Wittig reagent, e.g., one of the formula $R-CH_2-P^{\oplus}(C_6H_5)_3$ $Y^{\ominus}$ (VIII), that the obtained compound of Formula IV contains no or much less of the corresponding cis (Z) compound.

The obtained compounds of Formula IV are, for the most part, known; see the aforementioned references which disclose the compounds of Formula I. They may be deprotected by, for example, the reaction conditions given for Reaction CB and, when $R_{2z}$ is allyl, deallylated by, for example, the reaction conditions given for Reaction CA. When $R_{2z}$ is allyl, the two reactions may be performed in either order and sometimes, depending upon the $P_1$ groups, simultaneously. The resulting compounds are of Formula I. As set forth above, they may be converted by conventional means into the corresponding compounds of Formula I wherein $R_1$ hs a different significance as well as into the corresponding δ-lactones.

This invention is also directed to the synthesis of compounds of the formula

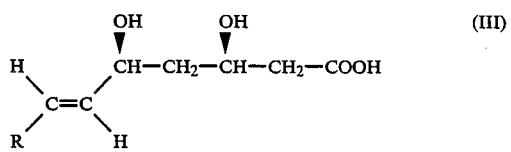

utilizing a compound of Formula VI wherein $R_{2z}$ is allyl by Reaction BB followed by Reactions CA and CB as set forth in detail in Reaction Schemes B and C. Each step of the process, both combinations of two consecutive steps and the entire three step process are within the scope of this invention.

A distinct advantage of this process is that the compounds of Formula III are obtained free or substantially free of the corresponding δ-lactones the presence of which may complicate purification of the compounds of Formula III. In addition, the deprotection reaction (Reaction CB) proceeds smoothly to give the compounds of Formula III in high yield.

While the compounds of Formulae III, IV, VI, XXXIII and XXXIV may be in racemic syn, i.e., erythro, form as well as in S[R*,S*], i.e., 3S,5R, enantiomeric form, they are preferably in R[R*,S*], i.e., 3R,5S, enantiomeric form.

The compounds of Formula III are compounds of Formula I wherein $R_1$ is hydrogen. They too may be converted by conventional means into the corresponding compounds of Formula I wherein $R_1$ is $R_2$ or M as well as into the corresponding δ-lactones. As set forth above, processes for so doing are disclosed in, for example, the aforementioned references that disclose the compounds of Formula I.

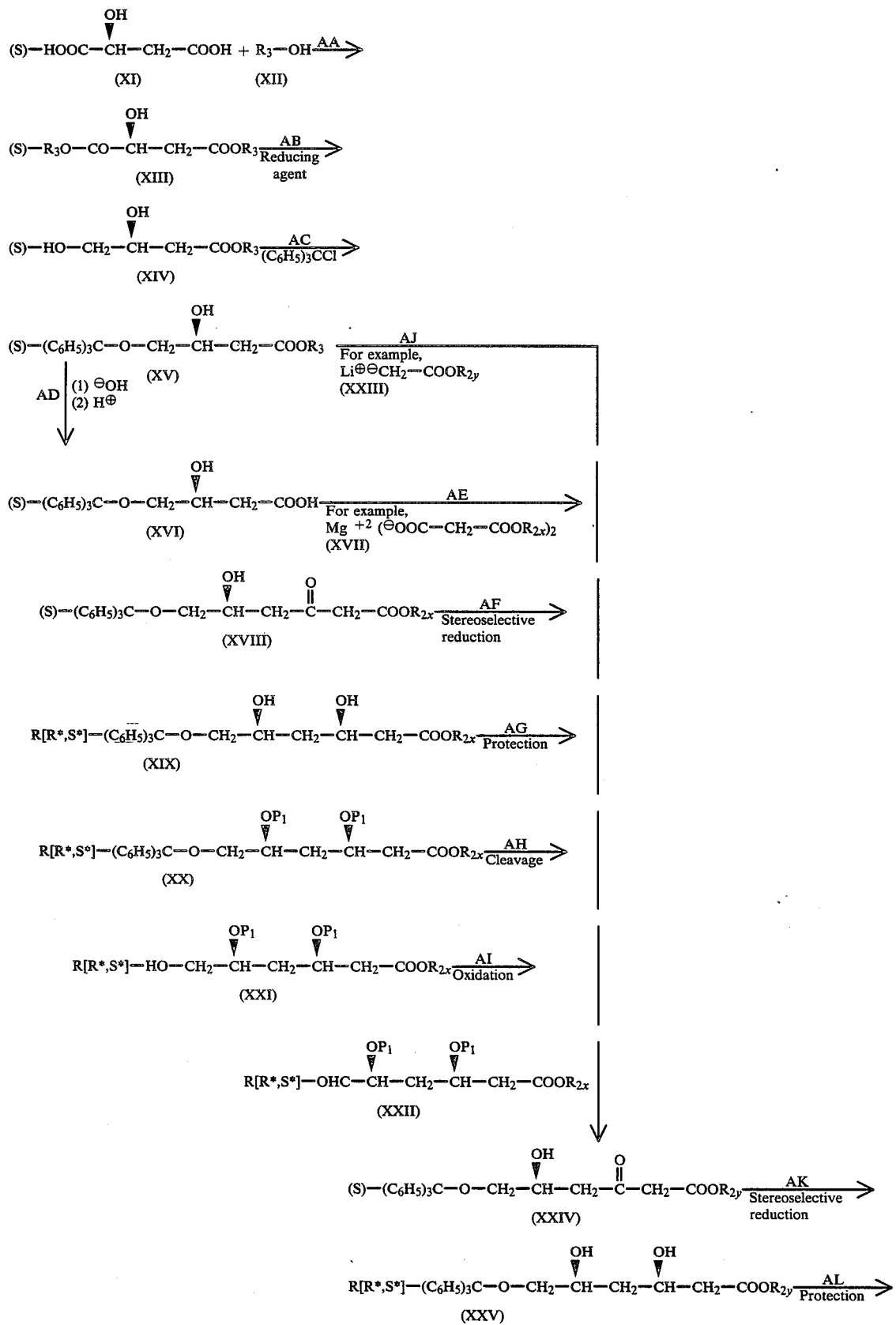

-continued
Reaction Scheme A

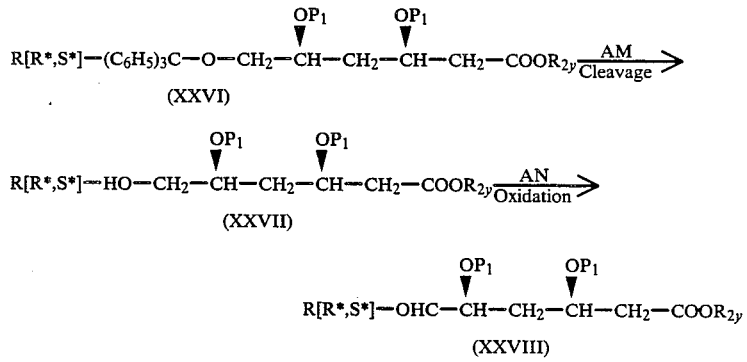

Reaction Scheme B

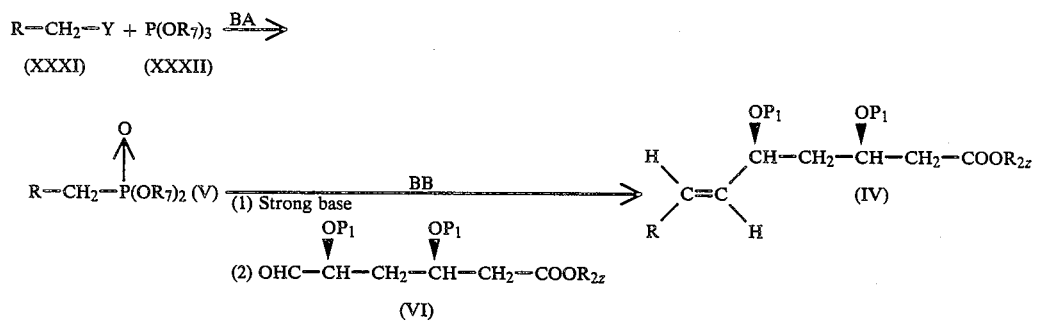

Reaction Scheme C

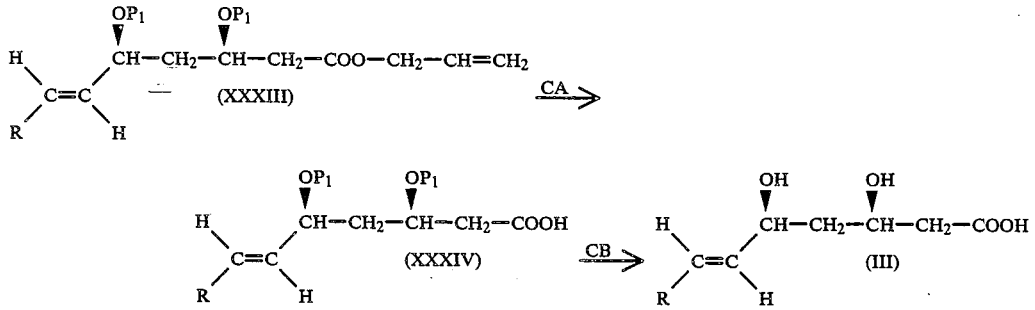

In Reaction Scheme A–C and throughout the balance of this specification:

Each $P_1$ is independently an hydroxy group-protecting group, preferably a trisubstituted silyl group, two or all three, more preferably all three, of the substituents of which are bulky, i.e., groups selected from (a) t-$C_{4-8}$alkyl, especially t-butyl and (b) aryl, aryl preferably being (1) phenyl; (2) phenyl substituted by 1 or 2 substituents selected from $C_{1-4}$alkyl, chloro, nitro and trifluoromethyl; or (3) phenyl substituted in the 4-position by (i) phenyl, (ii) benzyl or (iii) phenyl or benzyl substituted by 1 or 2 substituents selected from $C_{1-4}$alkyl, chloro, nitro and trifluoromethyl (the phenyl or benzyl group, when substituted, preferably being monosubstituted in the 4'-position). More preferably, (b) is phenyl or phenyl monosubstituted by $C_{1-4}$alkyl, chloro, nitro or trifluoromethyl. Any non-bulky substituent of a trisubstituted silyl group is preferably primary or secondary $C_{1-4}$alkyl, especially methyl. Preferably, the two $P_1$ groups are the same so that they can be introduced (and subsequently removed) at the same time. Also preferably, each $P_1$ is independently as trisubstituted silyl group having two aryl groups and one t-$C_{4-8}$alkyl group. More preferably, the preferences of the preceding two sentences occur simultaneously. Most preferably, each $R_1$ is diphenyl-t-butylsilyl.

$R_{2x}$ is primary or secondary $C_{1-4}$alkyl, benzyl or allyl, preferably $R_{2x}'$, where $R_{2x}'$ is primary or secondary $C_{1-4}$alkyl not containing an asymmetric carbon atom, benzyl or allyl, and most preferably $R_{2x}''$, where $R_{2x}''$ is methyl, ethyl or allyl.

$R_{2y}$ is $C_{1-4}$alkyl not containing an asymmetric carbon atom, preferably t-butyl.

$R_3$ is methyl or ethyl, preferably methyl.

Each $R_4$ is independently primary or secondary $C_{2-4}$alkyl.

Each $R_7$ is methyl or ethyl.

Y is chloro or bromo.

Each of the other variables is as set forth above.

| Reaction/Type | Reagents, Molar Ratios and Comments | Temperature | Time | Solvent | Inert Atmosphere |
|---|---|---|---|---|---|
| AA (Esterification) | Diesterify XI to obtain XIII, e.g., with: | | | | |
| | (1) At least 2 moles XII and 0.7-1 mole of an acidic compound, pref. acetyl chloride, per mole XI. Pref., commence reaction at 0°-4° C. and complete at 20°-25° C. | ~ −5°-25° C., pref. −5°-10° C., e.g., 0°-4° C.→ 20°-25° C. | 2-25 hrs. | Anhydrous excess XII | — |
| | (2) Adjust pH to 7-8 with base, e.g., sodium carbonate. | 0°-25° C. | 1-30 min. | Same as Step 1 | — |
| AB (Reduction) | Reduce XIII to XIV with reducing agent, e.g.: (1) Treat XIII with borane-dimethylsulfide complex and sodium borohydride, pref. 1-1.25 moles borane (as borane-dimethyl-sulfide complex) and catalytic amount, e.g., 0.01-0.1 mole, pref. 0.04-0.05 mole, sodium borohydride per mole XIII. | 10°-40° C., pref. 20°-25° C. | 1-4 hrs. | AIO, pref. ES, esp. THF | Yes |
| | (2) Quench with, for example, methanol. | 20°-25° C. | 1-30 min. | Same as Step 1 | — |
| AC (Etherification) | Etherify XIV to obtained XV, e.g., with: 1-1.5 moles triphenylmethyl chloride per mole XIV and 1-2 moles base, pref. an amine, esp. pyridine or triethylamine, per mole triphenylmethyl chloride. | 0°-50° C., pref. 20°-25° C. | 8-24 hrs. | AIO, pref. HLA, esp. methylene chloride | Yes |
| AD (Hydrolysis and Neutralization) | Hydrolyze XV with base and neutralize the obtained salt, e.g., with: | | | | |
| | (1) 1-2 moles base, pref. sodium hydroxide or potassium hydroxide, per mole XV. | 10°-80° C., e.g., 20°-25° C. | 1-4 hrs. | Mixture of water and IO, pref. mixture of water and THF, methanol or ethanol | — |
| | (2) Acidify, e.g., to pH 5-7, with an acid, pref. a weak acid such as citric acid. | 20°-25° C. | 1-30 min. | Same as Step 1 | — |
| AE | Convert XVI to XVIII utilizing, for example, XVII, e.g.: | | | | |
| | (1) 1 mole 1,1-carbonyldiimidazole per mole XVII to be used in Step 2. | 20°-25° C. | 2-6 hrs., pref. 4 hrs | AIO, pref. ES, esp. THF | Yes |
| | (2) 1-1.5 moles XVII per mole XVI. | 20°-25° C. | 8-24 hrs. | Same as Step 1 | Yes |
| | (3) Acidify to pH 2-6.5. | 20°-25° C. | 1-30 min. | Same as Step 1 | — |
| AF (Reduction) | Stereoselectively reduce the keto group to a hydroxy group without affecting balance of molecule, e.g., with: (1) 1-2.5 moles, pref. 1.02-1.5 moles, e.g., 1.02-1.3 moles, tri-(primary or secondary $C_{2-4}$alkyl)borane or (primary or secondary $C_{1-4}$alkoxy or allyloxy)-di-(primary or secondary $C_{2-4}$alkyl)borane per mole XVIII. Carry out under at least essentially anhydrous conditions. Pref. are triethylborane and tri-n-butyl-borane. | −80°-30° C., e.g., −70° C. or 20°-30° C. | 1-3 hrs. | Mixture of THF and allyl alcohl or $C_{1-4}$-alkanol (pref. a primary or secondary $C_{1-4}$-alkanol, esp. methanol), ratio of THF to alcohol (esp. methanol) pref. 3-6:1, esp. 3-4:1, by volume | Yes |
| | (2) 1-1.5 moles sodium borohydride per mole XVIII. After reaction, allow to warm to 0°-30° C., e.g., 20°-30° C., and quench with, e.g., saturated ammonium chloride solution. | −80°-70° C., e.g., −70° C. | 4-8 hrs. | Same as Step 1 | Yes |
| | (3) Alternative (a): Aqueous, e.g., 30%, hydrogen peroxide, pref. 4-8 moles, esp. 5-6 moles, hydrogen peroxide per mole XVIII and sufficient buffer to maintain pH 7-7.2. | −70°-25° C., pref. 20°-25° C. | 2-4 hrs. | Same as Step 1 or ethyl acetate | — |
| AF (Reduction) Cont'd. | Alternative (b): Large excess of methanol or ethanol, esp. methanol. It is convenient to azeotrope a solution of product of Step 2 in methanol three or four times. | 30°-80° C., e.g., 60°-80° C. | 0.5-5 hrs., pref. 1-4 hrs. | Neat | — |
| AG (Protection) | Protect hydroxy groups without affecting balance of molecule by reacting with at least 2 moles, pref. 2-3 moles, $P_1$-L (L is leaving group, e.g., chloro, bromo or p-tolylsulfonyl) and sufficient acid acceptor, if needed. | | | | |
| | When $P_1$'s are trisubstituted silyl groups, | 20°-100° C., | 16-24 hrs. | AIO, pref. | Yes |

-continued

| Reaction/Type | Reagents, Molar Ratios and Comments | Temperature | Time | Solvent | Inert Atmosphere |
|---|---|---|---|---|---|
| | 2-3 moles $P_1$-Cl per mole XIX and 1-3 moles imidazole per mole $P_1$-Cl. | pref. 60°-80° C., e.g., 60° C. | | dimethylformamide | |
| AH (Cleavage) | Cleave triphenylmethyl group with reagent to which the $P_1$ groups are stable without affecting balance of molecule. | | | | |
| | When $P_1$'s are trisubstituted silyl groups, treat XX with, e.g., acid, esp. trifluoroacetic acid (e.g., anhydrous or 70% aqueous). Commence at −78° C. and allow temperature to rise to 0° C. or 20°-25° C. or carry out at 20°-25° C. | −78°-25° C. | 2-4 hrs. | Inert, e.g., HLA, pref. methylene chloride | Yes |
| AI (Oxidation) | Oxidize hydroxymethyl group to aldehyde group without affecting balance of molecule with mild oxidizing agent, e.g., with: | | | | |
| | 1-3 moles, pref. 2-3 moles, esp. 2.5 moles, pyridinium chlorochromate and 0.5-2 kg. molecular sieves (pref. 4 Å.) per mole XXI. | 20°-25° C. | 1-3 hrs. | AIO, e.g., HLA, pref. methylene chloride | Yes |
| AJ | Convert XV to XXIV by, for example, reacting with XXIII. | | | | |
| | (1) Preparation of XXIII: 1-1.01 moles lithium diisopropylamide per mole $CH_3$—$COOR_{2y}$. | −80°-50° C., pref. −65°-50° C. | 0.5-1 hr. | AIO, e.g., Es, pref. THF | Yes |
| | (2) 3-5 moles, pref. 3.5-4 moles, XXIII (assuming 100% yield in Step 1) per mole XV. If necessary, complete reaction at −5°-5° C. | −80°-50° C., pref. −70°-60° C., or −65°-55° C. | 1-3 hrs. | Same as Step 1 | Yes |
| | (3) Quench with, e.g., saturated aqueous ammonium chloride solution. | 0°-25° C. | 1-30 min. | — | — |
| AK | Same as Reaction AF (Molar quantities are per mole XXIV) | Same as AF | Same as AF | Same as AF | Same as AF |
| AL | Same as Reaction AG (Molar quantities are per mole XXV) | Same as AG | Same as AG | Same as AG | Same as AG |
| AM | Same as Reaction AH (Molar quantities are per mole XXVI) | Same as AH | Same as AH | Same as AH | Same as AH |
| AN | Same as Reaction AI (Molar quantities are per mole XXVII) | Same as AI | Same as AI | Same as AI | Same as AI |
| BA | 1-1.1 moles XXXII per mole XXXI. Can use excess XXXII as the solvent. | 20°-140° C., pref. 80°-140° C., more pref. 110°-140° C. (not in excess of the reflux temperature) | 6-24 hrs., usually 10-18 hrs. | HC, e.g., benzene, toluene or xylene, or neat (excess XXXII is solvent) | Yes |
| BB (Wittig) | (1) 1 mole strong base, pref. a lower alkyllithium (more pref. n-butyllithium) or lithium diisopropylamide, and, optionally, lithium chloride (pref. 1.75-2 moles) per mole V. Pref. add strong base to other reactant(s). | −20°-0° C. | 0.5-1.5 hrs. | AIO, pref. ES, more pref. a cyclic ES, esp. THF | Yes |
| | (2) 1-1.2 moles VI per mole V used Step 1. | −30°-0° C., pref. −20°-0° C. | 1-12 hrs. | Same as Step 1 | yes |
| | (3) Quench with, e.g., ammonium chloride solution or acetic acid. | −10°-25° C. | 1-5 min. | — | — |
| CA (Deallylation) | (Deallylate XXXIII without affecting balance of molecule, e.g.: | | | | |
| | Treat XXXIII with a neutral soluble palladium compound, e.g., tetrakis(triphenylphosphinyl)palladium ($[(C_6H_5)_3P]_4Pd$), or palladium diacetate and triphenylphosphine, and a carbocylic compound, i.e., a carboxylic acid such as acetic acid or a carboxylate salt such as ammonium formate. | 20°-90° C., e.g., 20°-25° C. | 0.5-4 hrs. | AIO, pref. HLA, esp. methylene chloride, or ES, esp. cyclic ES such as THF or dioxane | Yes |
| CB (Deprotection) | Cleave $P_1$ groups without affecting balance of molecule. When $P_1$ groups are trisubstituted silyl groups, use, e.g.: | | | | |
| | 2-15 moles, pref. 4-12 moles, fluoride reagent, esp. tetra-n-butylammonium fluoride or trihydrate thereof, per mole XXXIV and 0.8-2 moles, pref. 1-1.5 moles, glacial acetic acid per mole fluoride reagent. First add glacial acetic acid to solution of XXXIV and then add fluoride reagent or add solution of XXXIV to solution of other reactants. | 20°-60° C., pref. 20°-25° C. | 2-72 hrs. | AIO, e.g., ES, pref. THF | Yes |

The products of Step 2 of Reaction AF are of the formula

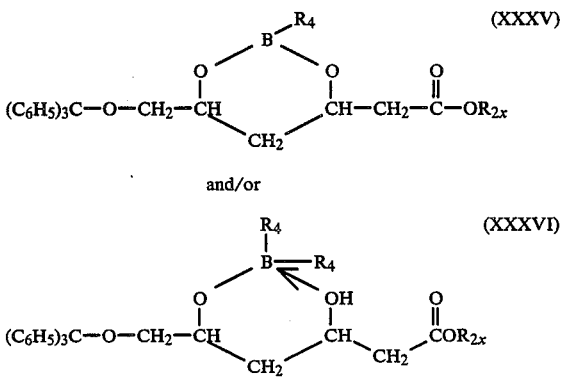

whereas those of Reaction AK are of the same formula(e) except that the $R_{2x}$ group is replaced by an $R_{2y}$ group.

In the preceding table,
AIO = anhydrous inert organic solvent
ES = either solvent, for example, diethyl ether, 1,2-diethoxyethane, 1,2-dimethoxyethane, tetrahydrofuran and mixtures thereof
esp. = especially
HC = hydrocarbon solvent, for example, benzene, toluene, xylene and mixtures thereof
HLA = halogenated lower alkane solvent, for example, carbon tetrachloride, chloroform 1,1-dichloroethane, 1,2-dichloroethane, methylene chloride and 1,1,2-trichloroethane, usually preferably methylene chloride
hr. (hrs.) = hour(s)
IO = inert organic solvent
min. = minutes
pref. = preferably, preferred
THF = tetrahydrofuran.

Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the art to vary those that are not critical.

The reaction times set forth in the preceding table are also merely exemplary and may be varied. As is well-known, the reaction time is often inwardly related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized. Unless otherwise indicated, all solvent mixtures are by volume.

The term "inert atmosphere", as utilized in the preceding table, means an atmosphere that does not react with any of the reactants, intermediates or end products or otherwise interfere with the reaction. While a carbon dioxide atmosphere is suitable for certain reactions, the inert atmosphere is usually nitrogen, helium, neon, argon or krypton, or a mixture thereof, and most often dry nitrogen to maintain anhydrous conditions. Most reactions, including those where the use of an insert atmosphere is not specified, are carried out under an inert atmosphere, usually dry nitrogen or argon, for convenience.

In the preceding table, n-butyllithium is preferably employed as a 1.3–1.7M. solution in hexane, and lithium diisopropylamide is preferablly prepared in situ from n-butyllithium and diisopropylamine.

The product of each reaction may, if desired, be purified by conventional techniques such as recrystallization (if a solid), column chromatography (e.g., utilizing a silica gel column), preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification.

The compounds of Formulae XI, XII, XVII, XXXI, XXXII and XXXIV and the reagents not designated by Roman numeral are known or, if unknown, may be synthesized by processes analogous to those described in the literature for similar known compounds.

For example, the compounds of Formula XXXI are disclosed in or synthesizable by the processes disclosed in the aforementioned references that disclose the compounds of Formula I.

The compounds of Formula VI in R[R*,S*] form are synthesized as disclosed in Reaction Scheme A; those in racemic erythro form are synthesized by the process described in U.S. Pat. No. 4,571,428. Allyl alcohol may be used in process (e) thereof to obtain the corresponding allyl esters. See also Steps 1 and 2 of Example 2 of this specification.

The compounds of Formula XVII are advantageously synthesized by reacting a comound of the formula HOOC—$CH_2$—$COOR_x$ (XXXVII) with magnesium methoxide, the molar ratio of the former to the latter preferably being 2:1, in an at least substantially anhydrous inert polar solvent, e.g., tetrahydrofuran, at, for example, 20°–25° C. The compounds of the formula HOOC—$CH_2$—$COOR_{2x}$ are known.

The (primary or secondary $C_{1-4}$alkoxy or allyloxy)-di-(primary or secondary $C_{2-4}$alkyl)boranes utilized in Reactions AF and AK are disclosed in Koster et al., Ann. 1975, 352, and Chen et al., Tetrahedron Letters 28, 155 (1987). However, they may be prepared in situ from the corresponding tri-(primary or secondary $C_{2-4}$alkyl)-boranes by reaction with a primary or secondary $C_{1-4}$alkanol or allyl alcohol, the concentration of the former in the latter preferably being 0.2–1.2M, especially 0.5M.

The entire specifications of parent applications Ser. Nos. 06/857,689 and 07/023,079, particularly pages 1-24 and 43-46 of the former and 1-26 and 50-53 of the latter, are hereby incorporated by reference as if set forth herein in their entirety.

Throughout this specification, all temperatures are in degrees centigrade and room temperature (R.T.) is 20°-30° C., usually 20°-25° C., unless otherwise indicated, evaporations are done under vacuum employing minimal heating, drying of organic phases is done over anhydrous magnesium sulfate, unless otherwise indicated, silica gel is utilized for all column chromatographies, unless otherwise indicated, THF is tetrahydrofuran, DMF is dimethylformamide, TFA is trifluoroacetic acid, and TP is tetrakis(triphenylphosphinyl)palladium.

The following examples are illustrative of the invention.

PREPARATION 1

Magnesium bis-(nono-allyl malonate)

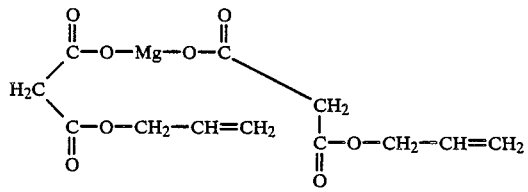

Step 1, Mono-allyl mono-acid malonate

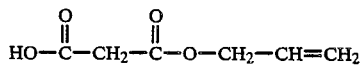

8 ml. of 2N. aqueous potassium hydroxide was added to a solution of 2.908 g. (15.8 mmol.) of diallyl malonate in 8 ml. of allyl alcohol at 0°. The reaction mixture was stirred at room temperature for two hours at which time the pH of the solution was 7 to 8. The solution was concentrated under reduced pressure, and the residue was diluted with ether and water. The organic layer was discarded, and the aqueous layer was acidified with 2N. hydrochloric acid to pH 2-3, saturated with solid sodium chloride and extracted with ethyl acetate. The combined organic layers were washed once with 20 ml. of saturated aqueous sodium chloride solution, dried over anhyd. sodium sulfate and filtered. Removal of the organic solvent under reduced pressure afforded 2.043 g. of the title mono-ester of this step.

Step 2, Magnesium bis-(mono-allyl malonate)

6.693 g. (46.5 mmol.) of the mono-ester of Step 1, above, was dissolved in 116 ml. of dry THF and 2 g., (23.2 mmol.) of magnesium methoxide was added at room temperature. The mixture was stirred for one hour, and the solvent was evaporated at reduced pressure to give 7.163 g. of the title product.

Repeating the procedure of this preparation but starting with an approximately equivalent amount of
(a) diethyl malonate or
(b) dimethyl malonate
in place of the diallyl malonate and in place of the allyl alcohol
(a) ethanol or
(b) methanol,
there is analogously obtained
(a) magnesium bis-(monoethyl malonate) and
(b) magnesium bis-(monoethyl malonate), respectively, which are used in Example 1, below.

PREPARATION 2

[[1-(4'-Fluorophenyl)-4-isopropyl-2-phenyl-1H-imidazol-5-yl]methyl]phosphonic acid dimethyl ester

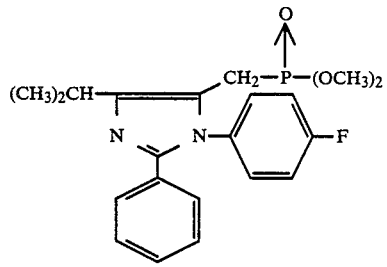

A solution of 310.5 g. of 1-(4'-fluorophenyl)-4-isopropyl-2-phenyl-1H-imidazole-5-methanol in 1.25 l. of methylene chloride is cooled to 0° C., and 178.4 of thionyl chloride is added over a period of several minutes, while maintaining an internal temperature of 10° C. The reaction mixture is stirred at room temperature for about 16 hrs. Under a reduced pressure of 30-50 mm. and a maximum internal temperature of 40°-45° C. as much of the solvent as possible is removed by distillation, 250 ml. of toluene is added, and the distillation is continued. is added at atmospheric pressure, and the 200 ml. of toluene mixture is heated to 90°-95° C. Over a period of 30-60 minutes, 1.32 kg of trimethylphosphite is slowly added, and the reaction mixture is heated to and held at reflux for two hours. The distillable solvents are removed by distillation at 20-40 mm. To the resulting solid residue is added 250 ml. of toluene and the distillation is continued until no further distillate can be recovered. The resulting solid is crystallized from 1.1 of toluene to obtain 233 g. of the title product, m.p. 139°-142° C.

PREPARATION 3

[[1-(3',5'-Dimethylphenyl)-3-methyl-2-naphthalenyl]-methyl]phosphonic acid dimethyl ester

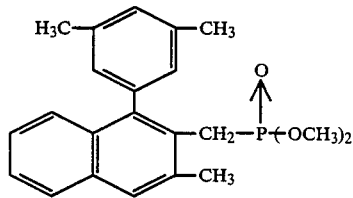

To 21 ml. of methylene chloride is added 16.7 g. of 1-(3',5'-dimethylphenyl)-3-methyl-2-naphthalene-methanol. The reaction mixture is cooled to 17° and 4.6 g. of thionyl chloride is added slowly while maintaining a maximum internal temperature of 24°. The reaction mixture is stirred for 2 hours, and the solvent is then distilled at 20-30 mm. and an external temperature of 65° to obtain a residual thick oil. To the residue is added 50 ml. of toluene and the distillation is continued until all of the solvent is recovered. The addition of toluene and the distillation are repeated two more times. To the resulting thick oil is added 35 ml. of trimethylphosphite. The reaction mixture is heated to reflux (115°-120°) and refluxed for 20 hours. The reaction mixture is then concentrated under reduced pressure until no trimethylphosphite can be recovered by distillation. 30 ml. of heptane is added, and the distillation is continued under reduced pressure. The addition of heptane is repeated several times. All solvents are distilled to obtain the crude title product as an orange solid residue. The residue is crystallized from heptane to obtain 16 g. of the title product, m.p. 132°-135°.

PREPARATION 4

Dimethyl [[1-isopropyl-3-(4'-fluorophenyl)indol-2-yl]methyl-phosphonate

To a mixture of 2.5 ml. of dimethylformamide and 500 ml. of dry THF is added 50 g. of 3-(4'-fluorophenyl)-1-isopropyl-1H-2-indolemethanol. Over a period of 20 minutes, 50 ml. of oxalyl choride is added while maintaining a maximum temperature of 25° and the reaction mixture is stirred at R.T. for two hours.

Under a reduced pressure of 20-30 mm. and an external temperature of 40° C. as much solvent as possible is recovered by distillation. 250 ml. of toluene is added, and the distillation is continued until no more solvent distills off.

100 ml. of trimethyl phosphite is added, and the reaction mixture is heated to reflux and refluxed for 1.5 hours. Under a reduced pressure of 20-30 mm. Hg, the solvent is distilled 250 ml. of toluene is added, and the distillation is continued until no more solvent distills off, leaving an oily residue. 39 g. of the title product is obtained by crystallization of the oil from hexane, m.p. 94°-96°.

EXAMPLE 1

Ethyl R[R*,S*]-3,5-di-(diphenyl-t-butylsilyloxy)-6-oxohexanoate

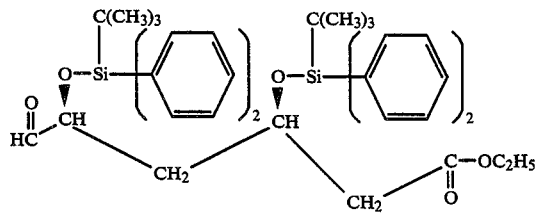

Step 1, Dimethyl L(—)malate (Reaction AA)

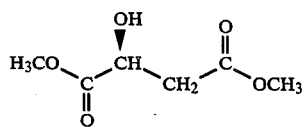

Into a vessel charged with 1356 ml. of methanol, 67.8 ml. of acetyl chloride was added dropwise at 3°-4° C. The resulting solution was stirred for one hour at 0°, and 176 g. of L-malic acid was added in portions over a period of 35 minutes. The reaction mixture was stirred at 0° C. for 2 hours and for about 18 hours at room temperature and then concentrated in vacuo. The residue was distilled under vacuum to obtain the title product of this step (173.82 g. (b.p. 78°-86° C./0.77 mm.)).

Step 2, Methyl (S)-3,4-dihydroxybutanoate (Reaction AB)

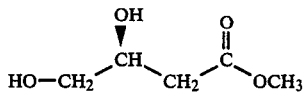

To a vessel charged with 19.2 g. (0.12 mole) of the hydroxy-diester of Step 1, above, in dry THF (250 ml.) was added dropwise 12.2 ml. of a 10M. solution of borane-dimethyl sulfide (0.122 mol.), under a nitrogen atmosphere, and the mixture was stirred at 16°-20° for 0.5 hour (which evolved hydrogen gas). 0.2 g. of NaBH₄ (6 mmol.) was added to the mixture, and the resulting solution was stirred for an additional 0.5 hour. During this period the temperature was increased from 20° to 35°. 77 ml. of dry methanol was added, and the reaction mixture was stirred for 0.5 hour. The solvent was removed by aspirator first and then under reduced pressure to obtain 17.34 g. of the crude product of this step, which was purified by column chromatography (5×18.5 cm.) using ethyl acetate/hexane (2:1) as the initial eluant and ethyl acetate as the final eluant to obtain 14.566 g. of the pure title product of this step.

Step 3, Methyl (S)-3-hydroxy-4-(triphenylmethoxy)butanoate (Reaction AC)

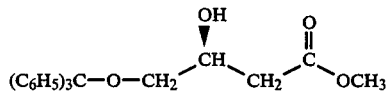

To 25.75 g. (0.192 mol.) of the product of Step 2, above, dissolved in 257 ml. of pyridine was added dropwise 56.25 g. (0.201 mol.) of trityl chloride dissolved in 172 ml. of methylene chloride at 0°. The reaction mixture was warmed to room temperature and stirred for about 16 hours. Removal of the solvent under reduced pressure gave a residue which was dissolved in ethyl acetate. The organic layer was washed with 2N. hydrochloric acid to remove pyridine, washed with saturated aqueous sodium bicarbonate, dried over anhyd. magnesium sulfate and filtered. The solvent was evaporated to obtain the crude title product of this step, which was pointed by column chromatography using ethyl acetate/hexane (1.18) as the eluant to obtain 61.4 g, of the title product of this step as a solid, $[\alpha]_D^{25} = -4°$ (c=1.0, CH₂Cl₂).

Step 4, (S)-3-Hydroxy-4-(triphenylmethoxy)butanoic acid (Reaction AD)

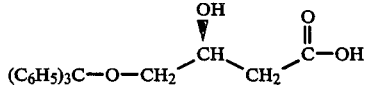

7.227 g. (19.22 mmol.) of the hydroxyester product of Step 3 was dissolved in 20 ml. of THF at 0° and 20 ml. of 1N. aqueous sodium hydroxide solution (20 mmol.) was added dropwise at 0°. The resulting solution was warmed to and stirred at room temperature for two hours (at which time TLC indicated no starting material). The solution was neutralized with citric acid (25 ml., 28% in water solution). The aqueous layer was extracted three times with 150 ml. portions of methylene chloride. The combined organic layers were dried over anhyd. magnesium sulfate to obtain the product of this step, which was used directly in the next step.

Step 5, Ethyl
(S)-5-hydroxy-3-oxo-6-(triphenylmethoxy-hexanoate (Reaction (AE)

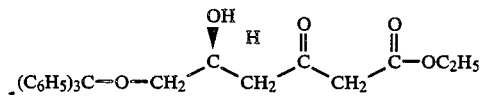

0.685 g. (4.228 mmol.) of 1,1-carbonyldiimidazole was added to a solution of 1.392 g. (3.84 mmol.) of the hydroxy-acid product of Step 4, above, in 19.2 ml. of anhydrous THF at 0°. The resulting solution was stirred at room temperature for four hours, 1.218 g. (4.228 mmol.) of Mg (OOC—CH$_2$—COOC$_2$H$_5$)$_2$ was added at the same temperature, and the reaction mixture was stirred for about 16 hours. The solvent was evaporated under reduced pressure. The residue was dissolved in ethyl acetate, and the solution was acidified with 11 ml. of 25% citric acid solution. The organic layer was separated, and the aqueous layer was extracted with another 90 ml. of ethyl acetate. The combined organic layers were washed twice with 25 ml. portions of aqueous sodium bicarbonate (10%) or until the aqueous layer became basic, dried over anhyd. magnesium sulfate and filtered. The solvent was removed under reduced pressure to obtain the crude title product of this step which was purified by column chromatography using ethyl acetate/hexane (1:4) as the eluant to yield 0.725 g. of the title product of this step, $[\alpha]_D^{25}$ —10.4° (c=1.38, CH$_2$C$_2$).

Step 6, Ethyl
R[R*,S*]-3,5-dihydroxy-6-(triphenylmethoxy)hexanoate (Reaction AF)

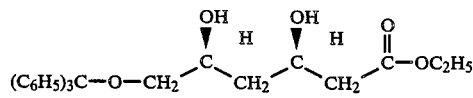

0.429 g. (0.988 mmol.) of the hydroxy-keto-ester product of Step 5, above, dissolved in 8 ml. of anhydrous THF and 2 ml. ethanol was mixed with 2.2 ml. of 1M. triethylborane (in hexane) at room temperature. (No heat was generated.) The resulting solution was stirred at room temperature for two hours, and then 41.61 mg. of sodium borohydride was added at −78°. The reaction mixture was stirred at room temperature for 5 hours. (TLC shows there was a trace of starting material.) The solution was poured into a solution of 17.24 ml. ethanol, 17.24 ml. of pH 7.00 buffer solution and 8.62 ml, of 30% aqueous hydrogen peroxide at −70° C. The mixture was allowed to warm to R.T. and was stirred for half an hour at R.T. Most of the organic solvent was evaporated under reduced pressure. The residue was extracted twice with portions of methylene chloride, and the combined organic layers were dried over anhydrous magnesium sulfate, filtered and evaporated to obtain the crude title product of this step which was purified by column chromatography to yield the pure title diol-ester of this step (348 mg.), $[\alpha]_D^{25}$=−4.72° (c=2.75, CH$_2$Cl$_2$) (about 98% enantiomerically pure).

Repeating this step but using in place of triethylborane, an approximately equivalent amount of monomethoxy-diethylborane, the same product is obtained (about 98% enantiomerically pure).

Step 7, Ethyl
R[R*,S*]-3,5-di-(diphenyl-t-butylsilyloxy)-6-(triphenylmethoxy)hexanoate (Reaction AG)

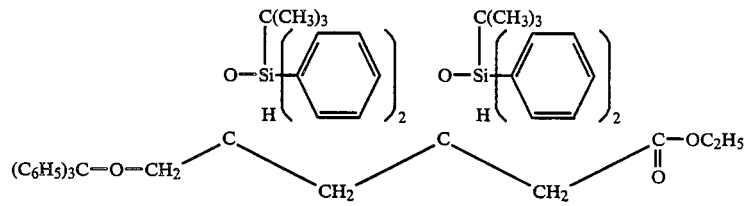

0.263 g. (0.6 mmol.) of the diol-ester product of Step 6, above, was dissolved in 2.5 ml. of DMF and 0.205 g. (5 equivalents) of imidazole was added. The mixture was stirred for ten minutes, and 0.373 g. (1.32 mmol.) of t-butyl-diphenylsilyl chloride was added dropwise to the solution by syringe. After being stirred for 4 hours, the reaction mixture was heated to 60° and stirred for 18 hours. The mixture was diluted with ethyl acetate and washed three times with water. The organic layer was dried over anhydrous magnesium sulfate and filtered. Removal of the solvent gave the crude title product of this step, which was purified by column chromatography using ethyl acetate/hexane (1:25) as the eluant to obtain 480 mg. of purified title product of this step, $[\alpha]_D^{25}$=−24.553° (c=2.24, CH$_2$Cl$_2$).

Step 8, Ethyl R[R*,S*]-3,5-di-(diphenyl-t-butylsilyloxy)-6-hydroxyhexanoate (Reaction AH)

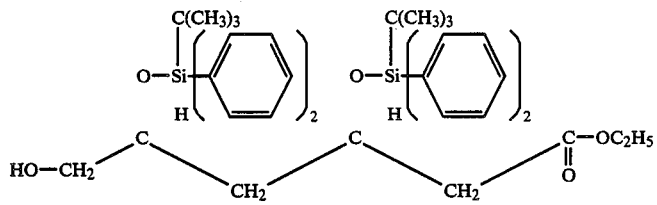

0.433 g. (0.486 mmol.) of the disilyloxy product of Step 7, above, is dissolved in 5 ml. of methylene chloride and 0.5 ml. of 70% aqueous trifluoroacetic acid (v/v) at −78°. After completion of the addition, the reaction mixture was warmed to 0° and stirred at that temperature for three hours. The reaction mixture was diluted with ethyl acetate and washed with saturated aqueous sodium bicarbonate solution. Removal of the organic solvent gave the crude title product of this step, which was diluted with hexane to precipitate triphenylmethanol not contaminated by any of the desired product. The solid was filtered, and the mother liquid was concentrated in vacuo to yield a crude mixture which was purified by column chromatography using ethyl acetate/hexane (1:10) as the eluant to obtain 0.272 g. of the title product of this step, $[\alpha]_D^{25} = -7.8°$ (c=2.5, $CH_2Cl_2$).

Step 9, Ethyl R[R*,S*]-3,5-di-(diphenyl-t-butylsilyloxy)-6-oxohexanoate (Reaction AI)

0.239 g. (0.357 mmol.) of the hydroxy product of Step 8, above, was dissolved in 2.5 ml. of methylene chloride. 0.48 g. of molecular sieves (4 Å.) was added to the solution, and then 0.24 g. (1.11 mmol.) of pyridinium chlorochromate was added to the reaction mixture at room temperature. The resulting mixture was stirred at room temperature for one hour and placed on the top of a filter funnel containing Celite and the product was eluted with methylene chloride to obtain 215 mg. of the title product of this example, $[\alpha]_D^{25} = 1.31°$ (c=0.76, $CH_2Cl_2$).

Repeating the procedure of this example but in Step 5 using in place of the magnesium bis-(monoethyl malonate) an approximately equivalent amount of:

(a) magnesium bis-(monoallyl malonate) or
(b) magnesium bis-(monomethyl malonate) (obtained by Preparation 1 above), and employing in place of the ethanol in Step 6, an equivalent amount of:

(a) allyl alcohol or
(b) methanol, respectively, there is accordingly obtained:

(a) allyl R[R*,S*]-3,5-di-(diphenyl-t-butylsilyloxy)-6-oxohexanoate, and
(b) methyl R[R*,S*]-3,5-di-(diphenyl-t-butylsilyloxy)-6-oxohexanoate, respectively.

EXAMPLE 2

1,1-Dimethylethyl R[R*,S*]-3,5-di-[(1′,4′-dimethylethyl)diphenylsilyloxy]-6-oxohexanoate

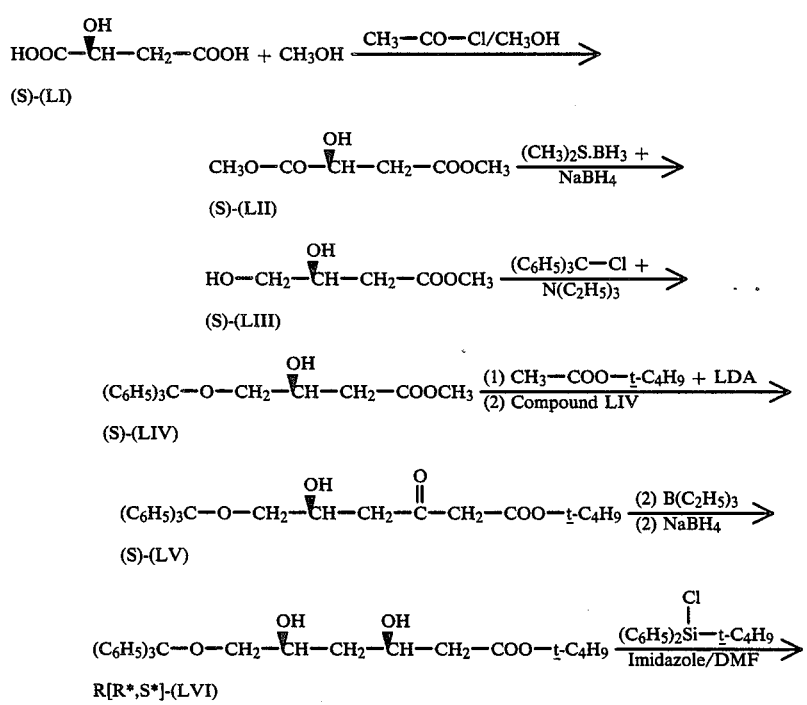

-continued

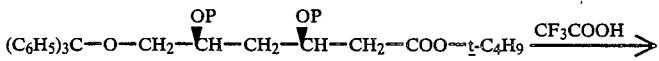

R[R*,S*]-(LVII)

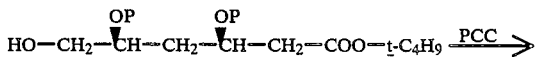

R[R*,S*]-(LVIII)

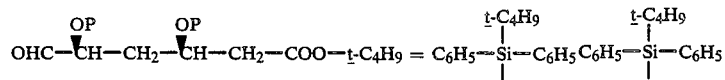

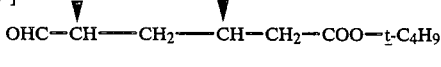

(LIX)

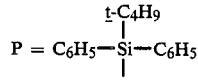

Step 1 (Reaction AA)

Dimethyl (S)-2-hydroxybutanedioate (Compound LII)

(a) 750 g. (9.6 moles) of acetyl chloride is added over a period of 30 minutes to 13.5 l. of methanol stirred at −5°–0° C. while maintaining an internal temperature of 0°–2° C. (the addition being very exothermic), the reaction mixture is stirred at 0° C. for 1 hour, 1.76 kg. (13.1 moles) of (S)-2-hydroxybutanedioic acid is added over a period of 30 minutes while maintaining an internal temperature of 0°–2° C. (the addition being slightly exothermic), and the reaction mixture is stirred at 0°–2° C. for 2 hours and at 20°–25° C. for 16 hours, the reaction mixture being stirred under nitrogen throughout. 898 g. (8.47 moles) of anhydrous sodium carbonate is added over a period of 15 minutes while maintaining an internal temperature of 20°–25° C. to adjust the pH to 7–8 (the addition being slightly exothermic), and the reaction mixture is stirred at 20°–25° C. for 30 minutes and filtered. The filter cake is washed twice with 500 ml. portions of methanol, the filtrate and washings are combined, and the solution is evaporated at 25–30 mm. Hg while maintaining an internal temperature of 35°–40° C. to a volume of about 2.5 l. and filtered. The filter cake is washed with 500 ml. of methanol, the filtrate and washing are combined, and the solvent is distilled at 25–35 mm. Hg and an internal temperature of 40° C. to obtain the crude product (2.22 kg.).

(b) A solution of 300 g. of crude product from Part (a) of this step in 300 ml. of methylene chloride is added to a slurry of 300 g. of 70-230 mesh A.S.T.M. silica gel in 1.4 l. of methylene chloride, and the product is eluted with 7–8 l. of methylene chloride. The methylene chloride is distilled at 30–40 mm. Hg and an external temperature of 50° C. to obtain the partially purified product which is vacuum distilled at 0.6 mm. Hg and an internal temperature of 96°–98° C. to obtain the 96.7% pure product (239 g.). B.p. 90°–92° C./1.5–2 mm. Hg, 78°–80° C./0.6 mm. Hg.

(c) The remainder of the crude product is similarly purified.

Step 2 (Reaction AB)

Methyl (S)-3,4-dihydroxybutanoate (Compound LIII)

7.5 g. (0.2 mole) of sodium borohydride is added in one portion to a mixture of 523 ml. of 10M. borane-dimethylsulfide complex (5.23 moles borane) and 1.8 l. of dry tetrahydrofuran stirred at 20°–25° C., the reaction mixture is stirred at 20°–25° C. for 30 minutes, a solution of 744 g of 94% pure Compound LII (4.31 moles) in 1.2 l. of dry tetrahydrofuran is added over a period of 1 hour while maintaining with external cooling at 3°–5° C. an internal temperature of 20–25° C. (the reaction is very exothermic, and hydrogen is evolved), and, after the exotherm stops, the reaction mixture is stirred at 20°–25° C. for 1 hour and cooled to 20° C., the reaction mixture being stirred under nitrogen throughout. 1.8 l. of methanol is slowly added while maintaining an internal temperature of 20°–25° C. (The first third of the addition is very exothermic and foaming occurs.) The reaction mixture is stirred for 30 minutes while maintaining an internal temperature of 20°–25° C., the solvent is distilled at 20–30 mm. Hg and an external temperature of 40°–45° C., 500 ml. of toluene is added, the solvent is distilled at 20–30 mm. Hg and an external temperature of 40°–45° C., an additional 500 ml. of toluene is added, and the solvent is distilled at 20–30 mm. Hg and an external temperature of 40°–45° C. to obtain the crude (89.7% pure) product as a very thick stirrable oil (633 g.). The entire reaction and the solvent distillations must be vented through bleach to trap any escaping dimethylsulfide.

Step 3 (Reaction AC)

Methyl (S)-3-hydroxy-4-(triphenylmethoxy)butanoate (Compound LIV)

(a) A solution of 1.82 kg. (6.53 moles) of triphenylmethyl chloride in 2.5 l. of methylene chloride is added over a period of 12 minutes to a mixture of 716 g. of 81.7% pure Compound LIII (4.40 moles), 880 g. (8.7 moles) of triethylamine and 4.9 l. of methylene chloride stirred at 15° C. while maintaining an internal temperature of 15°–20° C. (the addition being exothermic), and the reaction mixture is stirred at 23° C. for 16 hours, stirred at an internal temperature of 38°–40° C. for 15 minutes (during which gas evolves) and cooled to 25° C., the reaction mixture being maintained under nitrogen throughout. 7.4 l. of water is added, the bottom organic layer is separated, the aqueous layer is extracted with 500 ml. of methylene chloride, the methylene chloride extract is combined with the bottom organic layer, and the combined organic layers are washed successively with 7.4 l. of water, 7.4 l. of saturated sodium bicarbonate solution and 3.7 l. of water and filtered to remove any insolubles. The solvent is distilled at 20–30 mm. Hg and a maximum external temperature of 50°–60° C. to obtain a thick dark stirrable oil. 2.5 l. of methanol is added with stirring at 50° C., and the mixture is stirred at 50° C. for 5 minutes, cooled to 20° C. and filtered. The filter cake is washed with 1 l. of methanol, the filtrate and washing are combined, and the solvent is distilled at 20–30 mm. Hg and an external temperature of about 50° C. to obtain the crude product as a thick stirrable brown oil (1.75 kg.).

(b) A 90 cm.×13 cm. chromatographic column is charged with 7.2 l. of 1:2 ethyl acetate/mixed hexanes, 450 g. of sea sand is added, a slurry of 4 kg. of 70–230 mesh A.S.T.M. silica gel in 12 l. of 1:2 ethyl acetate/mixed hexanes is added while draining some of the solvent from the bottom of the column, sufficient solvent to lower the liquid level to the top of the silica gel is drained from the column, a solution of 1.0 kg. of the crude product of Part (a) of this step in 1.0 l. of methylene chloride is added, sufficient solvent to lower the liquid level to the top of the silica gel is drained from the column, the column is eluted with 18 l. of 1:2 ethyl acetate/mixed hexanes to obtain six fractions, and the column is eluted with 12 l. of 1:1 ethyl acetate/mixed hexanes to obtain eight fractions containing relatively pure product. These eight fractions are combined, the solvent is distilled at 20–30 mm. Hg and 60° C. to obtain a thick stirrable oil, 1 l. of isopropanol is added, the solvent is distilled at 20–30 mm. Hg and a maximum internal temperature of 60° C., an additional 1 l. of isopropanol is added, the solvent is distilled at 20–30 mm. Hg and a maximum internal temperature of 60° C., and the residue is added to 2 l. of isopropanol. The resulting solution is cooled to 0°–5° C. and maintained at this temperature for 3–4 hours. The solid is collected by filtration, washed twice with 250 ml. portions of cold (0°–5° C.) isopropanol and vacuum dried at 50°–60° C. to constant weight to obtain the 94.9% pure product (473 g.), m.p. 80°–82° C., $[\alpha]_{589}^{25} = -5.52°$ (c=1.5580, $CH_2Cl_2$). All chromatography fractions and mother liquors containing impure product may be combined and rechromatographed, etc. to obtain additional product.

(c) The balance of the crude product is similarly purified.

Step 4 (Reaction AJ)

1,1-Dimethylethyl (S)-5-hydroxy-3-oxo-6-(triphenylmethoxy)hexanoate (Compound LV)

1.98 l. of 1.6M. n-butyllithium/hexane (3.17 moles) is added over a 30 minute period to a mixture of 321 g. (3.17 moles) of diisopropylamine and 1.5 l. of dry tetrahydrofuran stirred at −50°−−40° C. during which the internal temperature rises to −5°-0° C., the pale yellow solution is stirred at −5°-0° C. for 30 minutes and cooled to −65° C., 367 g. (3.16 moles) of t-butyl acetate is added over a period of 40 minutes while maintaining an internal temperature of −63°−−60° C. (the addition being exothermic), the reaction mixture is stirred at −62°−−60° C. for 40 minutes, a solution of 300 g. (0.80 mole) of 95+% pure Compound LIV in 1.35 l. of dry tetrahydrofuran is added over a period of 25 minutes while maintaining an internal temperature of −62°−−58° C. (the addition being exothermic), and the reaction mixture is stirred at −62°−−58° C. for 1 hour, warmed to −5°-0° C., over a period of 45 minutes and stirred at −5°-0° C. for 30 minutes, the reaction mixture being stirred under nitrogen throughout. 1.8 l. of saturated ammonium chloride solution is added over a period of 3 minutes while maintaining an internal temperature of below 15° C. (the addition being exothermic), the mixture is stirred at 10°–15° C. for 10 minutes, 2.1 l. of toluene is added, and the top organic layer is separated, washed three times with 1.5 l. portions of water and, if any insolubles are present, filtered. The solvent is distilled at 20–30 mm. Hg and an internal temperature of 50°–60° C. to obtain the crude (87.1% pure) product as a very thick yellow oil that is stirrable at 50° C. (415 g.).

Step 5 (Reaction AK)

1,1-Dimethylethyl R[R*,S*]-3,5-dihydroxy-6-(triphenylmethoxy)hexanoate (Compound LVI)

A mixture of 715 ml. of 1M. triethylborane/tetrahydrofuran (715 mmoles), 4.76 l. of dry tetrahydrofuran and 1.44 l. of methanol is stirred at 18°–22° C. for 45 minutes and cooled to −75° C., a solution of 254.4 g of crude (90% pure) Compound LV (0.497 mole) in 960 ml. of dry tetrahydrofuran is added over a period of 15 minutes while maintaining an internal temperature of −75°−−72° C., the reaction mixture is stirred at −76°−−75° C. for 1 hour, 24.96 g. (0.66 mole) of sodium borohydride is added in portions over a period of 15 minutes while maintaining an internal temperature of −76°−−72° C., and the reaction mixture is stirred at −77°−−76° C. for 4.5 hours, the reaction mixture being stirred under nitrogen throughout. 756 ml. of saturated ammonium chloride solution is slowly added over a period of 25 minutes while maintaining an internal temperature of −76°−−67° C. (the addition is exothermic, and some forming occurs), the mixture is stirred at −68°−−67° C. for 30 minutes and warmed to 10°–15° C. over a period of 30 minutes, 360 ml. of water is added, the mixture is extracted with 3.6 l. of ethyl acetate, the top organic layer is separated and washed successively with 750 ml. of a 1:1 mixture of water and saturated sodium chloride solution and 750 ml. of saturated sodium chloride solution, and the solvent is distilled at 20–30 mm. Hg and a maximum external temperature of 50° C. 180 ml. of ethyl acetate is added, the solvent is distilled at 20–30 mm. Hg and a maximum external temperature of 50° C., and these two steps are repeated once. 2.91 l. of ethyl acetate is added to the obtained thick oil (the cyclic boronate), 290 ml. of 30% hydrogen peroxide solution (2.84 moles) is slowly added over a period of 20–30 minutes while maintaining an internal temperature of 20°–25° C. (the addition initially being exothermic), and the reaction mixture is stirred at 20°–25° C. for 2.5 hours and added to 360 ml. of water. The top organic layer is separated, washed three times (for 10–15 minutes each time) with 480 ml. portions of cold (0°–5° C.) 10% sodium sulfite solution (until the organic layer is free of peroxide) while maintaining an internal temperature of 25° C. and washed successively with 480 ml. of saturated sodium bicarbonate solution, 480 ml. of water (any emulsion that forms will separate within about an hour) and 480 ml. of saturated sodium chloride solution. The top organic layer is separated, and the solvent is distilled at 20-30 mm. Hg and a maximum external temperature of 50°-60° C. 326 ml. of methanol is added, the solvent is distilled at 20-25 mm. Hg and an internal temperature of 50°-60° C., and these two steps are repeated four more times. 100 ml. of toluene is added, the solvent is distilled at 20-30 mm. Hg and an internal temperature of 60° C., and these two steps are repeated three more times. The obtained oil is heated for an additional 3-4 hours at 20-30 mm. Hg and 50°-60° C. to obtain the crude (66.8% pure) product (255 g.). (The ratio of the R[R*,S*] isomer to the S[R*,R*] isomer is about 69:1 although in other batches it was as low as about 23:1.)

Step 6 (Reaction AL)

1,1-Dimethylethyl R[R*,S*]-3,5-di-[(1',1'-dimethylethyl)diphenylsilyloxy]-6-(triphenylmethoxy)hexanoate (Compound LVII)

132.5 g. (1.95 moles) of imidazole is added to a mixture of 267 g. of crude (55.8% pure) Compound LVI (0.322 mole) and 900 ml. of N,N-dimethylformamide while maintaining an internal temperature of 23°-25° C., the mixture is heated to 70°-72° C., 235.8 g. (0.86 mole) of t-butyldiphenylchlorosilane is added over a period of 2 minutes, and the reaction mixture is stirred at 70°-72° C. for 18 hours and cooled to 10° C., the reaction mixture being stirred under nitrogen throughout. The reaction mixture is added to a mixture of 2.5 l. of hexane and 1.1 l. of water, the mixture is stirred for 5 minutes, the organic top layer is separated and washed twice with 1.1 l. portions of water, and the solvent is distilled at 20-30 mm. Hg and an external temperature of 40°-60° C. to obtain the crude (62.8% pure) product (437.7 g.).

Step 7 (Reaction AM)

1,1-Dimethylethyl R[R*,S*]-3,5-di-[(1',1'-dimethylethyl)diphenylsilyloxy]-6-hydroxyhexanoate (Compound LVIII)

(a) A cold solution prepared from 960 g. of water, 600 g. of ice and 740 g. (6.49 moles) of trifluoroacetic acid is added over a period of 2 minutes to a solution of 432 g. of crude (62.8% pure) Compound LVII (0.29 mole) in 3.4 l. of methylene chloride while maintaining a maximum internal temperature of 25° C., and the reaction mixture is stirred at 22°-26° C. for 2.5 hours, the reaction mixture being stirred under nitrogen throughout. The organic bottom layer is separated and washed successively with 1.1 l. of saturated sodium bicarbonate solution and 1.0 l. of water, and the solvent is distilled at 20-30 mm. Hg and a maximum external temperature of 60° C. 100 ml. of mixed hexanes is added to the residue, the solvent is distilled at 20-30 mm. Hg and a maximum internal temperature of 60° C., and these two steps are repeated once, the distillation being continued until no more solvent distills off. 1.1 l. of mixed hexanes is added to the obtained thick semi-solid, the mixture is heated at 40°-45° C. for 10-15 minutes, cooled to 0°-5° C. and maintained at 0°-5° C. for 10 minutes, and the solid is collected by filtration and washed twice with 100 ml. portions of cold (10° C.) mixed hexanes. The filtrate and hexane washings are combined, and the solvent is distilled at 20-30 mm. Hg and an external temperature of 40°-60° C. to obtain the crude product as an oil (330 g.).

(b) The crude product of Part (a) is purified by HPLC using a Kiloprep 250 Millipore Process HPLC system with a reverse phase Kiloprep 250 $C_{18}$ cartridge (80 microns) and a 200 nm. detector. The column is flashed with methylene chloride until it is decontaminated (as indicated by the UV detector) and flushed with methanol for about 10 minutes and then with 9:1 methanol/water for about 6 minutes at a flow rate of 0.5 l./min. A solution of the crude product of Part (a) of this step in a mixture of 393 ml. of methanol and 22 ml. of water is placed on the column, and the column is eluted with 9:1 methanol/water for about 22 minutes, 11 minutes and 3 minutes to obtain fractions 1-3 and with methanol for about 4 minutes and 7 minutes to obtain fractions 4 and 5, the flow rate being 0.5 l./min. Fractions 4 and 5 are combined, the solvent is distilled at 20-40 mm. Hg and a maximum internal temperature of 40° C., 250 ml. of methylene chloride is added to the residue, the mixture is stirred at 30° C. for 5 minutes, the organic bottom layer is separated, and the solvent is distilled at 20-30 mm. Hg and a maximum internal temperature of 40°-45° C. 100 ml. of n-heptane is added, the solvent is distilled at 20-30 mm. Hg and 40°-45° C., and these two steps are repeated once. 460 ml. of n-heptane is added to the residue, and the mixture is heated to 80°-90° C. to dissolve the oil, allowed to cool to 20°-25° C. with stirring until solid forms and maintained at 10° C. for 2-3 hours. The resulting white solid is collected by filtration, washed twice with 50 ml. portions of cold (10° C.) n-heptane and vacuum dried to constant weight at 50° C. for 15 hours to obtain the 95.5% pure product as a white solid (122 g.). m.p. 79°-80° C., $[\alpha]_{589}^{20} = +8.35°$ (c=5.0, $CH_2Cl_2$). (The ratio of the R[R*,S*] isomer to the S[R*,R*] isomer is about 76:1.)

Step 8 (Reaction AN)

1,1-Dimethylethyl R[R*,S*]-3,5-di[(1',1'-dimethylethyl)diphenylsilyloxy]-6-oxohexanoate (Compound LIX)

150 g. (0.70 mole) of pyridinium chlorochromate is added over a period of 3 minutes to a mixture of 200 g. (0.28 mole) of 96.6% pure Compound LVIII, 2 l. of methylene chloride and 400 g. of 4 Å, powdered molecular sieves stirred at 20° C. while maintaining an internal temperature of 20°-22° C. (the addition being slightly exothermic), and the reaction mixture is vigorously stirred for 1 hour at 22°-25° C., the reaction mixture being stirred under nitrogen throughout. 3.32 l. of n-heptane is added, and the mixture is stirred at 23° C. for 5 minutes and filtered through 250 g. of Celite® filter air pre-wet with n-heptane. The filter cake is washed twice with 200 ml. portions of n-heptane, the filtrate and the n-heptane washings are combined, and the solvent is distilled at 20-30 mm. Hg and a maximum external temperature of 45°-50° C. 100 ml. of n-heptane is added, the solvent is distilled at 20-30 mm. Hg and a maximum external temperature of 45°-50° C., and this is repeated once. The resulting oil is dissolved in 400 ml. of 1:12 ethyl acetate/mixed hexanes and chromatographed on 420 g. of 70-230 mesh A.S.T.M. silica gel topped with about 2.5 cm. of sea sand utilizing a column having a 7 cm. inside diameter and 4 l. of 1:12 ethyl acetate/mixed hexanes as the eluant. The solvent is distilled at 20-30 mm. Hg and an external temperature of 50°-55° C. 100 ml. of n-heptane is added, the solvent is distilled at 20-30 mm. Hg and an external temperature of 50°-55° C., this is repeated once, and the residue is maintained at this pressure and temperature for 2 hours.

335 ml. of mixed hexanes is added at 40°-50° C. to the obtained thick oil, and the mixture is cooled to −35°−−30° C., seeded and maintained at −35°−−30° C. for 1 hour. The resulting white solid is collected by filtration, washed twice with 50 ml. portions of cold (−25°−−20° C.) mixed hexanes and dried to constant weight at 20-30 mm. Hg and 45°-50° C. for 24 hours to obtain the 99% pure product (175.2 g.), m.p. 81°-82° C., $[\alpha]_{589}^{25} = +5.21°$ (c=5.0, $CH_2Cl_2$). (The ratio of the R[R*,S*] isomer to the S[R*,R*] isomer is about 99:1.)

The stereochemistry of the product may also be designated as 3R,5S.

EXAMPLE 2A t-Butyl (S)-5-hydroxy-3-oxo-6-(triphenylmethoxy)hexanoate

Under a nitrogen atmosphere and at 0° C., 87.78 ml. of 1.5M. n-butyllithium/hexane (132 mmoles) is added dropwise to 18.49 ml. (132 mmoles) of diisopropylamine in 150 ml. of dry tetrahydrofuran, and the mixture is stirred for 30 minutes to form a solution of lithium diisopropylamide. The obtained solution is cooled to −70° C., a solution of 17.76 ml. (132 mmoles) of t-butyl acetate in 25 ml. of dry tetrahydrofuran is added over a period of 1 hour with stirring at −65°−−70° C., the reaction mixture is stirred for 1.5 hours at the same temperature, a solution of 11.28 g. (30 mmoles) of methyl (S)-3-hydroxy-4-(triphenylmethoxy)butanoate (obtainable by Step 3 of Example 1) in 75 ml. of dry tetrahydrofuran is added to the obtained solution of t-butyl lithioacetate at −65°−−70° C., and the yellow solution is stirred at about −70° C. for 0.5 hour, warmed to −10° C. and stirred at −10° C. for 1 hour (with thin layer chromatography (TLC) monitoring to indicate when the reaction is over), the reaction mixture being stirred under nitrogen throughout. 150 ml. of saturated aqueous ammonium chloride is added to quench the reaction at −60°−−70° C., the mixture is warmed to 0° C., transferred to a separatory funnel and diluted with ethyl acetate, and the organic phase is separated. The aqueous layer is extracted with an additional 200 ml. of ethyl acetate, and the organic phases are combined, washed successively with 90 ml. of 1N. hydrochloric acid and 90 ml. of saturated aqueous sodium bicarbonate, dried and filtered. The organic solution is evaporated to yield the crude product (17.43 g.) (estimated to be about 80% pure by chromatography analysis).

EXAMPLE 3

Sodium syn-(E)-7-[1'-isopropyl-3'-(4"-fluorophenyl)indol-2'-yl]-3,5-dihydroxyhept-6-enoate

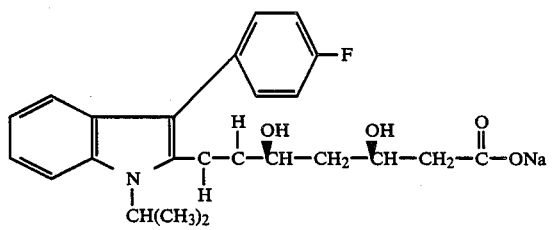

Step 1, Allyl (±)-syn-3,5-di-(diphenyl-t-butylsilyloxy)-6-hydroxy hexanoate

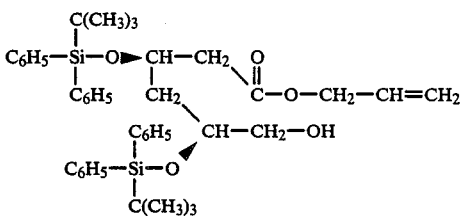

To 132 ml. of allyl alcohol is added 1 ml. of TFA and 30 g of cis-2-oxa-4,6-di-(diphenyl-t-butylsilyloxy)cycloheptanone (disclosed in U.S. Pat. No. 4,571,428 at Step D of Example 1). The mixture refluxed (internal temp. about 97°) for 5 to 6 hours and cooled to room temperature. The small amount of solid present is removed by filtration, and the filtrate is evaporated to dryness. To the residue is added water, and and the product is extracted with methylene chloride (separation is slow because of emulsion). The purified product is recovered from the extract by evaporating the solvent.

Step 2, Allyl (±)-syn-3,5-di-(diphenyl-t-butylsilyloxy)-6-oxohexanoate

To a vessel are added 1.36 g (2 mmol.) of the hydroxy-product of Step 1, above, 1.08 g. (5 mmol.) of pyridinium chlorochromate, 2.00 g. of 4 Å. molecular sieve powder and 30 ml. of methylene chloride, and the mixture is stirred at R.T. for 2 hours. The mixture is filtered through silica gel, and the filtrate evaporated to obtain the title aldehyde product of this step.

Step 3, Allyl (±)-syn-(E)-7-[1'-isopropyl-3'-(4"-fluorophenyl)indol-2'-yl]-3,5-di-(diphenyl-t-butylsilyloxy)hept-6-enoate (Reaction BB)

0.75 g. (2 mmol.) of [1'-isopropyl-3'-(4"-fluorophenyl)indol-2'-yl]methyl-phosphonic acid dimethyl ester obtained by Preparation 4, above, is dissolved in 5 ml. of dry THF, and the mixture is cooled to −20°. 1.4 ml. of 1.5M. n-butyllithium (in THF) is added, and the mixture is stirred at −20° for 20 minutes.

To the mixture is added, dropwise, 1.34 g. (2 mmol.) of (±)-syn-3,5-diol-(diphenyl-t-butylsilyloxy)-6-oxohexanoic acid allyl ester (of Step 2, above) in 3 ml. of dry THF, and the mixture is stirred for 5 hours at 0°.

The reaction mixture is diluted with 50 ml. of methylene chloride and washed with saturated aqueous ammonium chloride solution and the organic phase is dried over anhydrous magnesium sulfate and evaporated. The residual crude title product of this step is chromatographed on silica gel utilizing hexane/ethyl acetate (4:1) as the eluant to obtain the purified title product of this step (in about 50% yield).

Step 4, Syn-(E)-7-[1'-isopropyl-3'-(4"-fluorophenyl)indol-2'-yl]-3,5-di-(diphenyl-t-butylsilyloxy)hept-6-enoic acid (Reaction CA)

A mixture of 0.90 g. (1 mmol.) of the allyl ester of Step 3, above, 3 ml. of glacial acetic acid, 4 mg. of triphenylphosphine, 40 mg. of palladium tetra-(triphenylphosphine) and 3 ml. of methylene chloride is stirred at R.T. for 1 hr. and evaporated to dryness. The residue is chromatographed on silica gel using hexane/ethyl acetate (4:1) as the eluant to obtain the purified title product of this step (in about 56% yield).

Step 5, Sodium syn-(E)-7-[1'-isopropyl-3'-(4''-fluorophenyl)indol-2'-yl]-3,5-dihydroxyhept-6-enoate (Reaction CB)

20 ml. of 1M. tetrabutylammonium fluoride (in THF) is mixed with 1.2 ml. of glacial acetic acid. To the resulting solution 1.774 g. (2 mmol.) of the diprotected acid of Step 4 above is added, and the resulting mixture is stirred for about 50 hours at ambient temperature.

The reaction mixture is diluted with 200 ml. of ethyl acetate and washed four times with water. The organic phase is dried over anhyd. magnesium sulfate and evaporated. The residue is partitioned between water and hexane, and a solid results. The solid is the free acid of the title product and is recovered by filtration (in about 100% yield).

The free acid is converted to its sodium salt by conventional means.

Repeating the procedure of this example using in Step 3 the phosphonate esters of (a) Preparation 2, (b) Preparation 3 or (c) [1'-isopropyl-3'-(3'',5''-dimethylphenyl)indol-2'-yl]methyl-phosphonic dimethyl ester (prepared analogously), there is accordingly obtained (a) syn-(E)-7-[1'-(4''-fluorophenyl)-4'-isopropyl-2'-phenyl-1H-imidazol-5-yl]-3,5-dihydroxyhept-6-enoic acid and the sodium salt thereof, (b) syn-(E)-7-[1'-(3'',5''-dimethylphenyl)-3'-methyl-2'-naphthalenyl]-3,5-dihydroxyhept-6-enoic acid and the sodium salt thereof and (c) syn-(E)-7-[1'-isopropyl-3'-(3'',5''-dimethylphenyl)indol-2'-yl]-3,5-dihydroxyhept-6-enoic acid and the sodium salt thereof.

Repeating the procedure of this example, but using in place of the allyl (±)-syn-3,5-di-(diphenyl-t-butylsilyloxy)-6-oxohexanoate the R[R*,S*] chiral form obtainable by Example 1, there is accordingly obtained the title product of this example in R[R*,S*] chiral form.

EXAMPLE 4

Repeating the procedure of Step 4 of Example 3 but using in place of the glacial acetic acid/triphenylphosphine/palladium tetra-(triphenylphosphine) system used therein an equivalent amount of the systems of Table A and the variations in reaction conditions noted therein, the yields reported therein are obtained.

EXAMPLE 5

Sodium R[R*,S*]-(E)-7-[1'-(4''-fluorophenyl)-4'-isopropyl-2'-phenyl-1H-imidazol-5'-yl]-3,5-dihydroxyhept-6-enoate Repeating the procedure of Step 3 of Example 3 but using in place of the indolylphosphonate ester of Preparation 4 an approximately equivalent amount of the imidazolylphosphonate ester of Preparation 2 and in place of allyl (±)-syn-3,5-di-(diphenyl-t-butylsilyloxy)-6-oxohexanoate, an approximately equivalent amount of:

(a) allyl R[R*,S*]-3,5-di-(diphenyl-t-butylsilyloxy)-6-oxohexanate
(b) ethyl R[R*,S*]-3,5-(diphenyl-t-butylsilyloxy)-6-oxohexanoate
(c) methyl R[R*,S*]-3,5-di-(diphenyl-t-butylsilyloxy)-6-oxo-hexanoate (Example 1), or
(d) Compound LIX (Example 2, Step 8), there is accordingly obtained, respectively, the allyl, ethyl, methyl and t-butyl esters of R[R*,S*]-(E)-7-[1'-(4''-fluorophenyl)-4'-isopropyl-2'-phenyl-1H-imidazol-5'-yl]-3,5-di(diphenyl-t-butylsilyloxy)hept-6-enoic acid which, upon deprotection, respectively, yield the corresponding (a) allyl,
(b) ethyl,
(c) methyl and
(d) t-butyl ester forms of the title sodium salt, each of which upon saponification or hydrolysis followed by sodium salt formation in conventional manner, e.g., analogously to the process described in U.S. Pat. No. 4,571,428 and PCT Published Application WO 84/02131, yields the title product.

EXAMPLE 6

Sodium R[R*,S*]-(E)-7-[1'-isopropyl-3'-(4''-fluorophenyl)indol-2'-yl]-3,5-dihydroxyhept-6-enoate

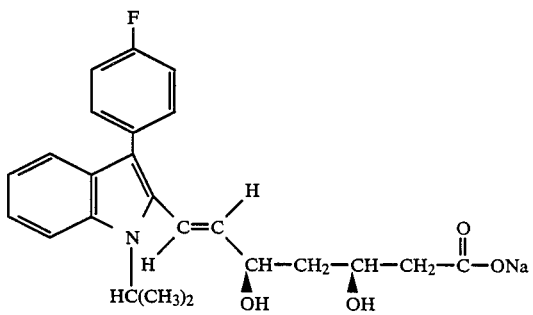

TABLE A

| Run No. | Pd Source | Carboxylate | Medium | Temperature | Time (Hours) | % Yield |
|---|---|---|---|---|---|---|
| 1 | TP | CH₃COOH | CH₂Cl₂ | RT. | 18 | About 50 |
| 2 | Pd(OCCH₃)₂ P(C₆H₅)₃ | HCOONH₄ | Dioxane | Reflux | 2 | 10 |
| 3 | TP | HCOONH₄ | Dioxane | Reflux | 1 | 85 |
| 4 | TP supported on polystyrene | HCOONH₄ | THF | Reflux | 18 | 85 |

Repeating the procedure of Step 3 of Example 3 but using in place of allyl (±)-syn-3,5-di-(diphenyl-t-butyl-silyloxy)-6-oxohexanoate an approximately equivalent amount of:
(a) allyl R[R*,S*]-3,5-di-(diphenyl-t-butylsilyloxy)-6-oxohexanoate
(b) ethyl R[R*,S*]-3,5-di-(diphenyl-t-butylsilyloxy)-6-oxohexanoate
(c) methyl R[R*,S*]-3,5-di-(diphenyl-t-butylsilyloxy)-6-oxohexanoate (Example 1) or
(d) Compound LIX (Example 2, Step 8), there is accordingly obtained, respectively, the allyl, ethyl, methyl and t-butyl esters of R[R*,S*]-(E)-7-[1'-isopropyl-3'-(4''-fluorophenyl)indol-2'-yl]-3,5-di-(diphenyl-t-butylsilyloxy)hept-6-enoic acid which, upon deprotection, respectively, yield the corresponding
(a) allyl,
(b) ethyl,
(c) methyl and
(d) t-butyl esters of the title sodium salt, each of which upon saponification or hydrolysis followed by sodium salt formation in conventional manner, e.g., analogously to the process described in U.S. Pat. No. 4,571,428 and PCT Published Application WO 84/02131, yields the title product.

EXAMPLE 7

Repeating Step 6 of Example 1 but carrying out the first stage for 5 hours at −70° C. (instead of 2 hours at room temperature), the title product of that step is similarly obtained.

EXAMPLE 8

Ethyl R[R*,S*]-3,5-dihydroxy-6-(triphenylmethoxy)hexanoate

To a vessel containing, at R.T. under an argon atmosphere, 180 ml. of dry THF and 45 ml. of methanol (dried over molecular sieves) is added 45 ml. of 1M. triethylborane in THF (45 mmol.). The resulting mixture is stirred for 15 minutes at R.T., cooled to −70° and stirred at −70° for 20 minutes, and over a period of 30 minutes 15.20 g. (35 mmol.) of ethyl (S)-5-hydroxy-3-oxo-6-(triphenylmethoxy)hexanoate in 60 ml. of dry THF and 15 ml. of dry methanol is added with stirring, the reactions mixture being maintained at −70° to −67°. After the addition is complete, the reaction mixture is stirred for 25 minutes at −70°.

1.47 g. of sodium borohydride (pellets) is added to the reaction mixture being maintained at −70° with stirring. About 3 minutes after the addition is completed, bubbling is observed and the mixture is stirred for 3 hours at −70°.

The reaction mixture is then quenched by addition of saturated aqueous ammonium chloride at −70° to −60°. 200 ml. of ethyl acetate is added, the mixture is allowed to slowly warm to R.T. The organic layer is separated, and the aqueous layer is extracted with 250 ml. of ethyl acetate. The combined ethyl acetate extracts are dried, filtered and evaporated to dryness.

HPLC grade methanol is added to the residual boronate complex, and the resulting mixture is azeotroped untilthe boronate complex is entirely converted to the title diol product (as indicated by TLC), additional methanol being added as needed. The title diol product is recovered by silica column chromatography (eluting with ethyl acetate/hexane (1:6)).

EXAMPLE 9

Repeating the procedure of Example 8 but starting with 240 ml. of dry THF, 60 ml. of dry methanol, 15.20 g. of ethyl (S)-5-hydroxy-3-oxo-6-(triphenylmethoxy)-hexanoate and 45 ml. of 1M. triethylborane (in THF) together in a vessel at about −70°, so that the room temperature stage is omitted, comparable results are obtained.

EXAMPLE 10

Repeating the procedures of Examples 8 and 9 but employing in place of the keto-hydroxy ethyl ester an equivalent amount of the t-butyl, methyl or allyl ester analog, comparable results are obtained.

What is claimed is:

1. A process for the synthesis of a compound of the formula

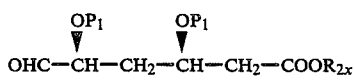

in R[R*,S*] enantiomeric form, wherein each
$P_1$ is independently an hydroxy group-protecting group, and
$R_{2x}$ is primary or secondary $C_{1-4}$alkyl, benzyl or allyl, comprising
(i) reacting the compound of the formula

in (S) enantiomeric form with a compound of the formula

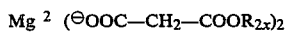

to obtain the corresponding compound of the formula

in (S) enantiomeric form,
(ii) stereoselectively reducing the obtained compound of the formula

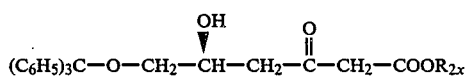

in (S) enantiomer form to obtain the corresponding compound of the formula

in R[R*,S*] enantiomeric form,
(iii) protecting the obtained compound of the formula

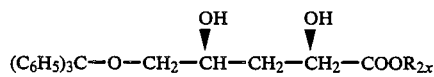

in R[R*,S*] enantiomeric form to obtain a corresponding compound of the formula

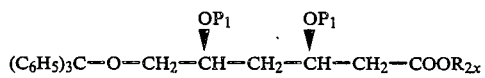

in R[R*,S*] enantiomeric form,
(iv) cleaving the triphenylmethoxy group of the obtained compound of the formula

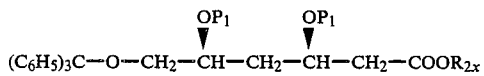

in R[R*,S*] enantiomeric form to obtain the corresponding compound of the formula

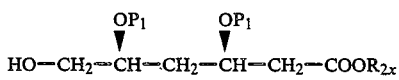

in R[R*,S*] enantiomeric form, and
(v) oxidizing the obtained compound of the formula

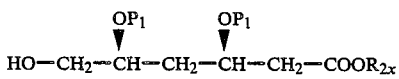

in R[R*,S*] enantiomeric form to obtain the corresponding compound of the formula

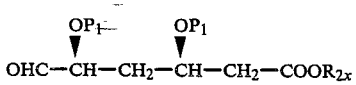

in R[R*,S*] enantiomeric form,
wherein each $P_1$ and $R_{2x}$ are as defined above.

2. A process according to claim 1 wherein $R_{2x}$ is methyl, ethyl or allyl.

3. A process according to claim 1 wherein each $P_1$ is a silyl group bearing three bulky substitutents, the two $P_1$ groups being the same.

4. A process according to claim 3 wherein each $P_1$ is a silyl group bearing two aryl groups and one alkyl group.

5. A process according to claim 4 wherein each $P_1$ is diphenyl-t-butylsilyl.

6. A process for the synthesis of a compound of the formula

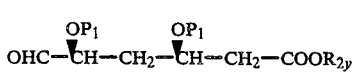

in R[R*,S*] enantiomeric form, wherein each
$P_1$ is independently an hydroxy group-protecting group, and
$R_{2y}$ is $C_{1-4}$alkyl not containing an asymmetric carbon atom,
comprising
(i) reacting a compound of the formula

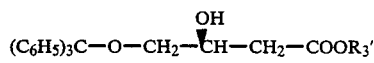

in (S) enantiomeric form with $Li^{\oplus \ominus}C$-$H_2$—$COOR_{2y}$ to form a compound of the formula

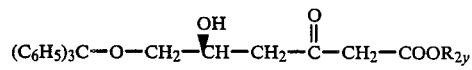

in (S) enantiomeric form,
(ii) stereoselectively reducing the obtained compound of the formula

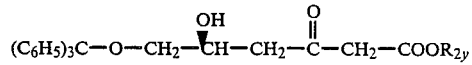

in (S) enantiomeric form to obtain the corresponding compound of the formula

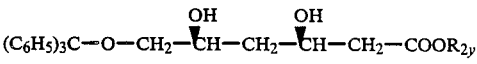

in R[R*,S*] enantiomeric form,
(iii) protecting the obtained compound of the formula

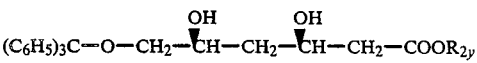

in R[R*,S*] enantiomeric form to obtain a corresponding compound of the formula

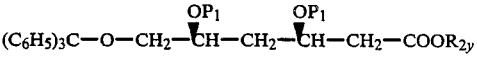

in R[R*,S*] enantiomeric form,
(iv) cleaving the triphenylmethoxy group of the obtained compound of the formula

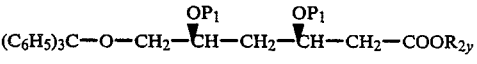

in R[R*,S*] enantiomeric form to obtain the corresponding compound of the formula

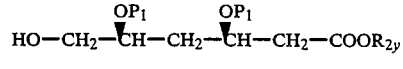

in R[R*,S*] enantiomeric form, and
(v) oxidizing the obtained compound of the formula

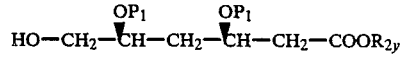

in R[R*,S*] enantiomeric form to obtain the corresponding compound of the formula

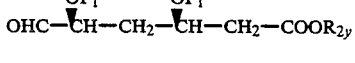

φin R[R*,S*] enantiomeric form,
wherein $R'_3$ is methyl or ethyl, and
each $P_1$ independently and $R_{2y}$ are as defined above.

7. A process according to claim 6 wherein $R_{2y}$ is t-butyl.

8. A process according to claim 6 wherein $R'_3$ is methyl.

9. A process according to claim 6 wherein each $P_1$ is a silyl group bearing three bulky substituents, the two $P_1$ groups being the same.

10. A process according to claim 9 wherein each $P_1$ is a silyl group bearing two aryl groups and one alkyl group.

11. A process according to claim 10 wherein each $P_1$ is diphenyl-t-butylsilyl.

12. A process according to claim 11 wherein $R_{2y}$ is t-butyl, and
$R'_3$ is methyl.

* * * * *